(12) United States Patent
Demmelmaier et al.

(10) Patent No.: US 9,718,042 B2
(45) Date of Patent: Aug. 1, 2017

(54) AROMATIZATION REACTORS WITH HYDROGEN REMOVAL AND RELATED REACTOR SYSTEMS

(71) Applicant: Chevron Phillips Chemical Company LP, The Woodlands, TX (US)

(72) Inventors: Cori A. Demmelmaier, Houston, TX (US); Daniel M. Hasenberg, Kingwood, TX (US); Scott H. Brown, Porter, TX (US); Vincent D. McGahee, Kemah, TX (US); Scott G. Morrison, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 14/757,790

(22) Filed: Dec. 23, 2015

(65) Prior Publication Data

US 2017/0183276 A1 Jun. 29, 2017

(51) Int. Cl.
| | |
|---|---|
| *B01J 8/00* | (2006.01) |
| *C07C 5/41* | (2006.01) |
| *B01J 8/02* | (2006.01) |
| *B01J 8/04* | (2006.01) |

(52) U.S. Cl.
CPC ............ *B01J 8/009* (2013.01); *B01J 8/0278* (2013.01); *B01J 8/0403* (2013.01); *B01J 8/0419* (2013.01); *C07C 5/41* (2013.01); *B01J 2208/027* (2013.01)

(58) Field of Classification Search
CPC ........ B01J 8/009; B01J 8/0419; B01J 8/0403; B01J 8/0407; C10G 59/02; C07C 5/41
See application file for complete search history.

(56) References Cited

U.S. PATENT DOCUMENTS

| | | | |
|---|---|---|---|
| 3,992,465 A * | 11/1976 | Juguin | ................... C10G 35/06 208/102 |
| 4,456,527 A | 6/1984 | Buss et al. | |
| 4,648,961 A | 3/1987 | Jacobson et al. | |
| 5,196,631 A | 3/1993 | Murakawa et al. | |
| 5,366,704 A | 11/1994 | Koves et al. | |
| 5,389,235 A | 2/1995 | Russ et al. | |
| 5,401,365 A | 3/1995 | Chen et al. | |
| 5,401,386 A | 3/1995 | Morrison et al. | |
| 5,866,743 A | 2/1999 | Heyes et al. | |
| 5,877,367 A | 3/1999 | Witte | |
| 5,931,987 A * | 8/1999 | Buxbaum | .............. B01D 53/22 55/524 |

(Continued)

FOREIGN PATENT DOCUMENTS

| | | |
|---|---|---|
| WO | WO 90/10685 | 9/1990 |
| WO | WO 2015/052297 | 4/2015 |

OTHER PUBLICATIONS

Ali et al., "Dehydrogenation of methylcyclohexane to toluene to a pilot-scale membrane reactor," Applied Catalysis A: General 155 (1997) pp. 41-57.

(Continued)

*Primary Examiner* — Lessanework Seifu
(74) *Attorney, Agent, or Firm* — Merchant & Gould P.C.

(57) ABSTRACT

The present invention discloses aromatization reactor vessels with hydrogen membrane tubes, and associated aromatization reactor vessel systems. Also disclosed are processes for conducting aromatization reactions utilizing these reactor vessels and systems.

20 Claims, 11 Drawing Sheets

(56) References Cited

U.S. PATENT DOCUMENTS

| | | | |
|---|---|---|---|
| 6,165,350 | A | 12/2000 | Lokhandwala et al. |
| 6,190,539 | B1 | 2/2001 | Holtermann et al. |
| 6,207,042 | B1 | 3/2001 | Holtermann et al. |
| 6,224,838 | B1 | 5/2001 | Schulz et al. |
| 6,350,371 | B1 | 2/2002 | Lokhandwala et al. |
| 6,406,614 | B1 | 6/2002 | Tiedtke et al. |
| 6,518,470 | B1 | 2/2003 | Fukunaga et al. |
| 6,544,408 | B1 * | 4/2003 | de Bonneville ....... B01J 8/0214 208/134 |
| 6,548,030 | B2 | 4/2003 | Heyes et al. |
| 6,592,749 | B1 | 7/2003 | Lokhandwala et al. |
| 6,812,180 | B2 | 11/2004 | Fukunaga |
| 7,153,801 | B2 | 12/2006 | Wu |
| 7,211,706 | B2 | 5/2007 | Gauthier et al. |
| 7,544,335 | B2 | 6/2009 | Scanlon et al. |
| 7,582,272 | B2 | 9/2009 | Glova et al. |
| 7,932,425 | B2 | 4/2011 | Blessing et al. |
| 8,119,203 | B2 | 2/2012 | Hise et al. |
| 9,085,736 | B2 | 7/2015 | Morrison et al. |
| 2011/0171117 | A1 | 7/2011 | Gorski et al. |
| 2013/0109897 | A1 | 5/2013 | Morrison et al. |
| 2015/0086472 | A1 | 3/2015 | Adamopoulos et al. |

OTHER PUBLICATIONS

Ali et al., "n-Heptane reforming in a system of reactors-interstage membrane to separate hydrogen," Applied Catalysis A: General 140 (1996) pp. 99-110.

Bayat et al., "Ultrapure Hydrogen Production via Dehydrogenation of Heavy Paraffin in a Linear Alkyl Benzenes Plant: Dynamic Modeling Study," ACS Publications, http://pubs.acs.org/doi/pdf/10.1021/ef5012462 (2014) 2 pages.

Gallucci et al., "Recent advances on membranes and membrane reactors for hydrogen production," Chemical Engineering Science 92 (2013) pp. 40-66.

Itoh et al., "Hydrogen recovery from cyclohexane as a chemical hydrogen carrier using a palladium membrane reactor," Catalysis Today 82 (2003) pp. 119-125.

Mostafazadeh et al., "A membrane catalytic bed concept for naphtha reforming in the presence of catalyst deactivation," Chemical Engineering and Processing 48 (2009) 683-694.

Ali et al., entitled *Exceeding Equilibrium Conversion with a Catalytic Membrane Reactor for the Dehydrogenation of Methylcyclohexane*, Chemical Engineering Science, 1994, vol. 49, No. 13, pp. 2129-2134.

* cited by examiner

US 9,718,042 B2

AROMATIZATION REACTORS WITH HYDROGEN REMOVAL AND RELATED REACTOR SYSTEMS

FIELD OF THE INVENTION

The present disclosure concerns hydrogen removal in reactor vessels and reactor systems, and more particularly relates to aromatization reactor vessels with membrane tubes for hydrogen removal and to reactor systems with integrated hydrogen removal systems.

BACKGROUND OF THE INVENTION

There are various techniques that can be used to remove hydrogen from reactor vessels and reactor systems. However, these techniques have drawbacks at the operating conditions of typical aromatization reactor vessels and reactor systems, particularly at reaction temperatures ranging from 350° C. to 600° C., and under long-term continuous operation. Therefore, it would be beneficial to have aromatization reactor vessels and reactor systems with efficient and effective hydrogen removal features. Accordingly, it is to these ends that the present disclosure is directed.

SUMMARY OF THE INVENTION

Various aromatization reactor vessels and reactor systems are described herein. In one embodiment, an aromatization reactor vessel can comprise (a) a reactor wall; (b) a catalyst bed positioned within the reactor vessel; (c) an outer annulus positioned between the reactor wall and an outer particle barrier, the outer particle barrier and the outer annulus surrounding the catalyst bed; (d) a reactor inlet for a feed stream; (e) a reactor outlet connected to a center pipe, the center pipe positioned in the reactor vessel and surrounded by the catalyst bed; and (f) a membrane tube configured to remove $H_2$, the membrane tube positioned in the reactor vessel, the membrane tube having an inner permeate side and an outer process side. A flow path for the feed stream can begin at the reactor inlet, continue to the outer annulus, proceed through the outer particle barrier and the catalyst bed, into the center pipe, and to the reactor outlet. The membrane tube can be positioned in the center pipe, in the catalyst bed, or in the outer annulus, as well as more than one of these locations.

In another embodiment, an aromatization reactor vessel is provided, and in this embodiment, the aromatization reactor vessel can comprise (a) a reactor wall; (b) a catalyst bed positioned within the reactor vessel; (c) an outer annulus positioned between the reactor wall and an outer particle barrier, the outer particle barrier and the outer annulus surrounding the catalyst bed; (d) a reactor inlet for a feed stream; (e) a reactor outlet connected to a center pipe, the center pipe positioned in the reactor vessel and surrounded by the catalyst bed; and (f) a membrane tube configured to remove $H_2$, the membrane tube positioned in the reactor outlet, wherein the membrane tube has an inner permeate side and an outer process side, the outer process side facing the reactor outlet. A flow path for the feed stream can begin at the reactor inlet, continue to the outer annulus, proceed through the outer particle barrier and the catalyst bed, into the center pipe, and to the reactor outlet.

Aromatization reactor vessels configured with a reverse flow direction also are encompassed herein. One such aromatization reactor vessel can comprise (a) a reactor wall; (b) a catalyst bed positioned within the reactor vessel; (c) an outer annulus positioned between the reactor wall and an outer particle barrier, the outer particle barrier and the outer annulus surrounding the catalyst bed; (d) a reactor inlet for a feed stream and connected to a center pipe, the center pipe positioned in the reactor vessel and surrounded by the catalyst bed; (e) a reactor outlet, which is connected to the outer annulus; and (f) a membrane tube configured to remove $H_2$, the membrane tube positioned in the reactor vessel, the membrane tube having an inner permeate side and an outer process side. A flow path for the feed stream can begin at the reactor inlet, continue to the center pipe, proceed through the catalyst bed and the outer particle barrier, into the outer annulus, and to the reactor outlet. Another aromatization reactor vessel with a reverse flow direction can comprise (a) a reactor wall; (b) a catalyst bed positioned within the reactor vessel; (c) an outer annulus positioned between the reactor wall and an outer particle barrier, the outer particle barrier and the outer annulus surrounding the catalyst bed; (d) a reactor inlet for a feed stream and connected to a center pipe, the center pipe positioned in the reactor vessel and surrounded by the catalyst bed; (e) a reactor outlet, which is connected to the outer annulus; and (f) a membrane tube configured to remove $H_2$, the membrane tube positioned in the reactor outlet, wherein the membrane tube has an inner permeate side and an outer process side, the outer process side facing the reactor outlet. A flow path for the feed stream can begin at the reactor inlet, continue to the center pipe, proceed through the catalyst bed and the outer particle barrier, into the outer annulus, and to the reactor outlet.

Embodiments of this invention also are directed to aromatization reactor vessel systems containing two or more reactor vessels configured in series, at least one of which is an aromatization reactor vessel with an integrated membrane tube, as described herein.

In yet another embodiment of this invention, an aromatization reactor vessel system is provided, and in this embodiment, the system can comprise (I) an aromatization reactor vessel and (II) a $H_2$ removal system. The aromatization reactor vessel can comprise (a) a reactor wall; (b) a catalyst bed positioned within the reactor vessel; (c) an outer annulus positioned between the reactor wall and an outer particle barrier, the outer particle barrier and the outer annulus surrounding the catalyst bed; (d) a reactor inlet for a feed stream; and (e) a reactor outlet connected to a center pipe, the center pipe positioned in the reactor vessel and surrounded by the catalyst bed. A flow path for the feed stream can begin at the reactor inlet, continue to the outer annulus, proceed through the outer particle barrier and the catalyst bed, into the center pipe, and to the reactor outlet. The $H_2$ removal system can be configured to remove $H_2$ from a reactor effluent, and the $H_2$ removal system can be positioned downstream of the reactor outlet. The $H_2$ removal system can comprise a shell containing a membrane tube, wherein the reactor effluent passes through the shell, and the membrane tube has an inner permeate side and an outer process side, the outer process side facing the shell.

Aromatization reactor vessel systems also can be configured for reverse flow and, therefore, such systems can comprise (I) an aromatization reactor vessel and (II) a $H_2$ removal system, in which the aromatization reactor vessel can comprise (a) a reactor wall; (b) a catalyst bed positioned within the reactor vessel; (c) an outer annulus positioned between the reactor wall and an outer particle barrier, the outer particle barrier and the outer annulus surrounding the catalyst bed; (d) a reactor inlet for a feed stream and connected to a center pipe, the center pipe positioned in the reactor vessel and surrounded by the catalyst bed; and (e) a reactor outlet, which is connected to the outer annulus. A flow path for the feed stream can begin at the reactor inlet, continue to the center pipe, proceed through the catalyst bed and the outer particle barrier, into the outer annulus, and to the reactor outlet. The $H_2$ removal system can be configured to remove $H_2$ from a reactor effluent, and the $H_2$ removal system can be positioned downstream of the reactor outlet. The $H_2$ removal system can comprise a shell containing a membrane tube, wherein the reactor effluent passes through the shell, and the membrane tube has an inner permeate side and an outer process side, the outer process side facing the shell.

Aromatization processes also are disclosed herein. Generally, these processes can comprise (i) introducing a feed stream comprising $H_2$ and a non-aromatic hydrocarbon (for example, naphtha) into the reactor inlet and the flow path of any of the reactor vessels or systems described herein; (ii) contacting the feed stream with an aromatization catalyst; (iii) catalytically converting at least a portion of the non-aromatic hydrocarbon within the reactor vessel to produce an aromatic hydrocarbon (for example, benzene, toluene, or xylenes) and $H_2$; (iv) discharging a reactor effluent comprising the aromatic hydrocarbon from the reactor vessel via the reactor outlet; and (v) removing a portion of the $H_2$ in the reactor vessel (or in the reactor outlet, or in the reactor effluent) via the membrane tube to reduce a partial pressure of $H_2$ in the process. In some embodiments, the $H_2$:hydrocarbon ratio can be reduced from about 4:1-5:1 to about 1.5:1-2:1.

Both the foregoing summary and the following detailed description provide examples and are explanatory only. Accordingly, the foregoing summary and the following detailed description should not be considered to be restrictive. Further, features or variations can be provided in addition to those set forth herein. For example, certain embodiments can be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present invention. In the drawings.

DEFINITIONS

Figure 1:
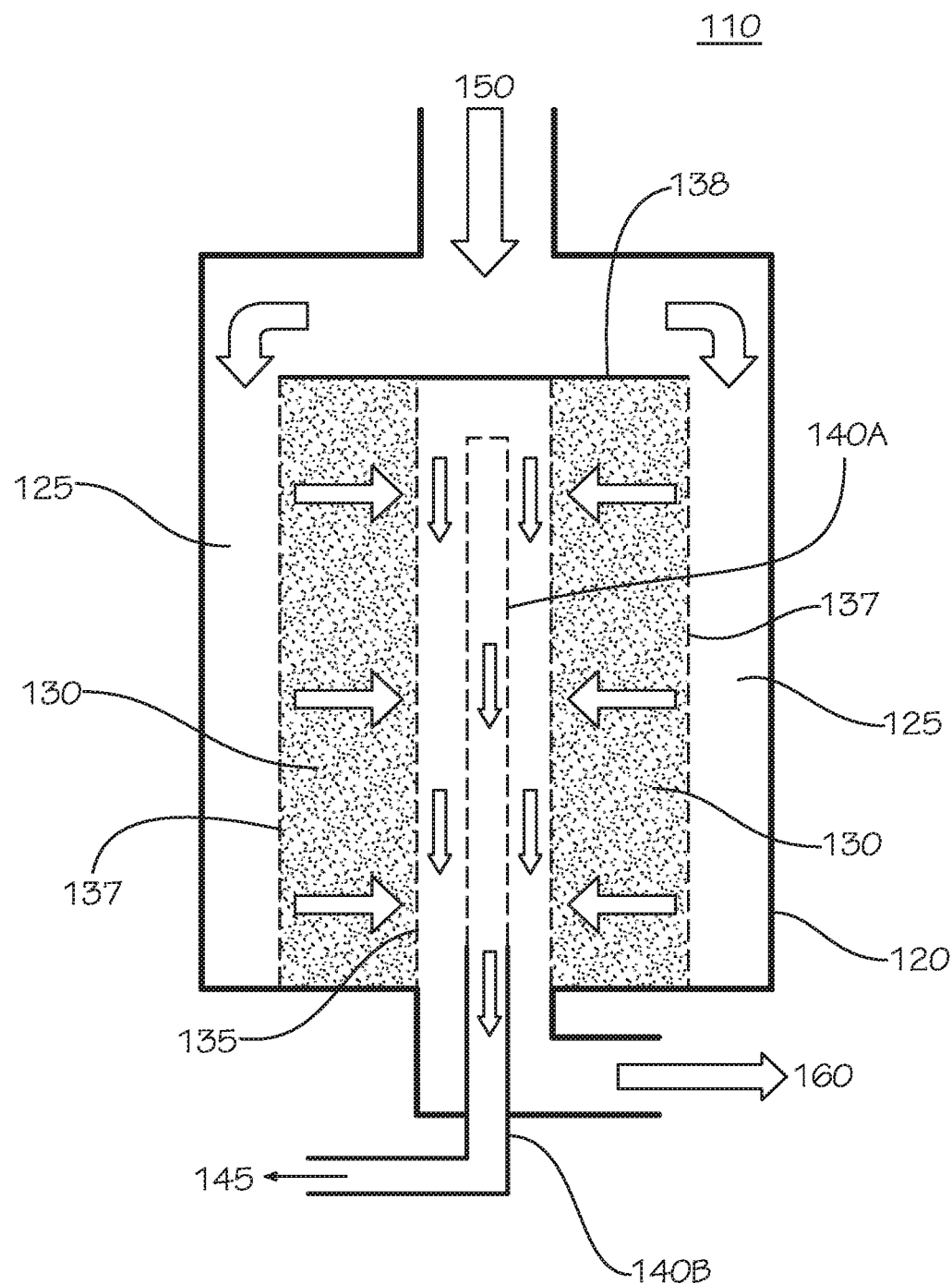
FIG. 1 illustrates a partial cross-sectional view of a reactor vessel with a membrane tube in a center pipe in an embodiment of the present invention.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects or embodiments, a combination of different features can be envisioned. For each and every aspect, embodiment, and feature disclosed herein, all combinations that do not detrimentally affect the designs, processes, or methods described herein are contemplated with or without explicit description of the particular combination. Additionally, unless explicitly recited otherwise, any aspect, embodiment, or feature disclosed herein can be combined to describe inventive features consistent with the present disclosure.

While apparatuses, systems, and processes are described herein in terms of "comprising" various components, devices, or steps, the apparatuses, systems, and processes can also "consist essentially of" or "consist of" the various components, devices, or steps, unless stated otherwise. For example, a feed stream consisting essentially of hydrogen and a non-aromatic hydrocarbon can include aromatic hydrocarbons typically present in a commercially produced or commercially available sample of a non-aromatic hydrocarbon.

The terms "a," "an," and "the" are intended to include plural alternatives, for example, at least one. For instance, the disclosure of "a reactor vessel" or "a transition metal" is meant to encompass one, or combinations of more than one, reactor vessel or transition metal, unless otherwise specified.

Unless explicitly stated otherwise in defined circumstances, all percentages, parts, ratios, and like amounts used herein are defined by weight.

Generally, groups of elements are indicated using the numbering scheme indicated in the version of the periodic table of elements published in Chemical and Engineering News, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular hydrocarbon or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to hexane includes n-hexane, 2-methyl-pentane, 2,2-dimethylpentane, 2,3-dimethylpentane, cyclohexane, and methylcyclopentane; and a general reference to a butyl group includes a n-butyl group, a sec-butyl group, an iso-butyl group, and a t-butyl group.

In one embodiment, a chemical "group" can be defined or described according to how that group is formally derived from a reference or "parent" compound, for example, by the number of hydrogen atoms removed from the parent compound to generate the group, even if that group is not literally synthesized in such a manner. These groups can be utilized as substituents or coordinated or bonded to metal atoms. By way of example, an "alkyl group" formally can be derived by removing one hydrogen atom from an alkane. The disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

As used herein, the term "hydrocarbon" refers to a compound containing only carbon and hydrogen atoms, and can be linear or branched unless otherwise specified. Other identifiers can be utilized to indicate the presence of particular groups, if any, in the hydrocarbon (for example, an aromatic hydrocarbon and a non-aromatic hydrocarbon, among others).

An "aromatic" hydrocarbon is a hydrocarbon containing a cyclically conjugated double bond system that follows the Hückel (4n+2) rule and contains (4n+2) pi-electrons, where n is an integer from 1 to 5. Aromatic hydrocarbons include benzene, toluene, and xylene. As disclosed herein, the term "substituted" can be used to describe an aromatic hydrocarbon wherein a non-hydrogen moiety formally replaces a hydrogen atom in the aromatic hydrocarbon, and is intended to be non-limiting, unless specified otherwise.

As used herein, the term "alkane" refers to a saturated hydrocarbon. Other identifiers can be utilized to indicate the presence of particular groups, if any, in the alkane (for example, halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. The alkane or alkyl group can be linear or branched unless otherwise specified. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups; additionally, the "alkyl group," "alkylene group," and "alkane group" can be linear or branched unless otherwise specified.

A "cycloalkane" is a saturated cyclic hydrocarbon, with or without side chains, for example, cyclobutane, cyclopentane, cyclohexane, methyl cyclopentane, and methyl cyclohexane. Other identifiers can be utilized to indicate the presence of particular groups, if any, in the cycloalkane (for example, halogenated cycloalkane indicates that the presence of one or more halogen atoms replacing an equivalent number of hydrogen atoms in the cycloalkane). Unsaturated cyclic hydrocarbons having one or more endocyclic double or triple bonds are called cycloalkenes and cycloalkynes, respectively. Cycloalkenes and cycloalkynes having only one, only two, and only three endocyclic double or triple bonds, respectively, can be identified by use of the term "mono," "di," and "tri within the name of the cycloalkene or cycloalkyne. Cycloalkenes and cycloalkynes can further identify the position of the endocyclic double or triple bonds.

As used herein, the term "alkene" refers to an unsaturated hydrocarbon. Other identifiers can be utilized to indicate the presence of particular groups, if any, in the alkene (for example, halogenated alkene indicates that the presence of one or more halogen atoms replacing an equivalent number of hydrogen atoms in the alkene). The alkene group can be linear or branched unless otherwise specified.

The term "non-aromatic" hydrocarbon whenever used in this specification and claims refers to a mixture of hydrocarbons. In an embodiment, the feed stream to the aromatization system can comprise hydrogen and a non-aromatic hydrocarbon. In an embodiment, the non-aromatic hydrocarbon can comprise linear or branched alkanes, cycloalkanes, or alkenes containing at least six carbon atoms. The non-aromatic hydrocarbon can comprise a mixture of hydrocarbons comprising $C_6$ to $C_8$ hydrocarbons containing up to about 10 wt. %, or alternatively up to about 15 wt. % of $C_5$ and lighter hydrocarbons ($C_5^-$), and containing up to about 10 wt. % of $C_9$ and heavier hydrocarbons ($C_9^+$). Such low levels of $C_9^+$ and $C_5^-$ hydrocarbons can maximize the yield of aromatics from the aromatization process. In some embodiments, an optimal non-aromatic hydrocarbon can maximize the percentage of $C_6$ hydrocarbons. These non-aromatic hydrocarbons can be prepared by separating a hydrocarbon such as naphtha into a light hydrocarbon fraction and a heavy hydrocarbon fraction, and using the light hydrocarbon fraction. In another embodiment, the non-aromatic hydrocarbons can comprise a naphtha. The naphtha can be a hydrocarbon with a boiling range of from about 70° F. (21.1° C.) to about 450° F. (232.2° C.). The naphtha can contain aliphatic, naphthenic, or paraffinic hydrocarbons.

The term "halogen" has its usual meaning. Examples of halogens include fluorine, chlorine, bromine, and iodine.

A catalyst fouling curve can be used to characterize the deactivation of an aromatization catalyst. A catalyst-fouling curve can be obtained by plotting the yield-adjusted temperature of the catalyst as a function of time. The slope of the plot is positive and represents increases in the reactor and catalyst temperature necessary to maintain a constant product yield. As will be understood by one of ordinary skill in the art, the specific definition of yield-adjusted temperature will depend on a variety of reaction conditions, such as, for example, the number of reactors employed in a given system and the specific target yield chosen. In an embodiment, the yield-adjusted temperature can be the temperature of an isothermal or adiabatic catalyst bed. Alternatively, the yield-adjusted temperature can be the catalyst temperature normalized to a specific level of catalyst productivity at a defined set of process conditions. Alternatively, the yield-adjusted temperature for an aromatization process can be the isothermal furnace set point temperature, corrected to a specific target yield of % aromatics in a final reactor effluent. This furnace set point temperature is normally the same as the bed inlet temperature. Alternatively, the yield-adjusted temperature for an adiabatic aromatization process can be the reactor inlet set point temperature, corrected for differences from a specific target yield of % aromatics in the overall final reactor effluent.

The term "about" means that amounts, sizes, formulations, parameters, and other quantities and characteristics are not and need not be exact, but can be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

Various numerical ranges are disclosed herein. When a range of any type is disclosed or claimed, the intent is to disclose or claim individually each possible number that such a range could reasonably encompass, including end points of the range as well as any sub-ranges and combinations of sub-ranges encompassed therein, unless otherwise specified. As a representative example, the present disclosure recites that an operating temperature of an aromatization reactor vessel can be in a range from about 260° C. to about 600° C. in certain embodiments. By a disclosure that the temperature can be in a range from about 260° C. to about 600° C., the intent is to recite that the temperature can be any temperature within the range and, for example, can be equal to about 260° C., about 300° C., about 350° C., about 400° C., about 450° C., about 500° C., about 550° C., or about 600° C. Additionally, the temperature can be within any range from about 260° C. to about 600° C. (for example, the temperature can be in a range from about 350° C. to about 550° C.), and this also includes any combination of ranges between about 260° C. and about 600° C. Likewise, all other ranges disclosed herein should be interpreted in a manner similar to this example.

The term "contacting" is used herein to describe processes and compositions wherein the components are contacted together in any order, in any manner, and for any length of time, unless otherwise specified. For example, the components can be contacted by blending or mixing. Further, unless otherwise specified, the contacting of any component can occur in the presence or absence of any other component of the processes and compositions described herein. Combining additional materials or components can be done by any suitable method. Further, "contacting" two or more components can result in a mixture, a reaction mixture, or a reaction product.

Although any methods, devices, and materials similar or equivalent to those described herein can be used in the practice or testing of the invention, the typical methods, devices, and materials are herein described.

All publications and patents mentioned herein are incorporated herein by reference for the purpose of describing and disclosing, for example, the constructs and methodologies that are described in the publications and patents, which might be used in connection with the presently described invention.

DETAILED DESCRIPTION OF THE INVENTION

The following detailed description refers to the accompanying drawings. Wherever possible, the same or similar reference numbers are used in the drawings and the following description to refer to the same or similar elements or features. While various embodiments of the invention are described, modifications, adaptations, and other implementations are possible. For example, substitutions, additions, or modifications can be made to the elements illustrated in the drawings, and the methods described herein can be modified by substituting, reordering, or adding stages to the disclosed methods. Accordingly, the following detailed description and its exemplary embodiments do not limit the scope of the invention.

Beneficially, the reactor vessels, reactor systems, and aromatization processes disclosed herein can employ the removal of $H_2$ via a membrane tube at standard aromatization reactor conditions. Thus, it is not required to remove $H_2$ and the other reactor contents for external and downstream treatment at non-reactor conditions, which would then require both gas/liquid separation processes and the use of significant energy for re-heating and returning the treated material to standard aromatization reactor conditions.

Aromatization Reactor Vessels and Systems

FIG. 1 illustrates an embodiment of an aromatization reactor vessel 110 consistent with the present invention. While not being limited thereto, the aromatization reactor vessel 110 is described herein as it pertains to its use in the catalytic conversion of a non-aromatic hydrocarbon to produce an aromatic hydrocarbon, examples of which include benzene, toluene, or xylene, as well as mixtures thereof. The aromatization reactor vessel 110 in FIG. 1 can include a reactor wall 120, a center pipe 135 surrounded by a catalyst bed 130, an outer particle barrier 137 surrounding the catalyst bed, and an outer annulus 125 between the outer particle barrier 137 and the reactor wall 120. The reactor vessel 110 can further include a reactor inlet 150 for feed stream, a top cover plate 138, and a reactor outlet 160 through which flows a reactor effluent stream. The reactor outlet 160 is connected to the center pipe 135 as shown in FIG. 1. The arrows in FIG. 1 illustrate a typical flow path for a feed stream entering the aromatization reactor vessel 110, for instance, starting at the reactor inlet 150, then directed to the outer annulus 125 by the top cover plate 138, then through the outer particle barrier 137 and the catalyst bed 130, into the center pipe 135, and finally to the reactor outlet 160 as reactor effluent. As disclosed herein, in other embodiments of this invention, the flow path can be reversed, and the inlet and outlet locations can be reversed.

In FIG. 1, the outer particle barrier 137 in the aromatization reactor vessel 110 can be formed in any number of ways, including employing scallops, outer baskets, and the like. An outer basket more closely resembles what is shown is FIG. 1. An outer basket can have a circular cross-sectional shape. The outer basket has openings that permit the passage of the feed stream, but not the passage of the catalyst particles. The passage of the feed stream can be accomplished by having slots formed into the outer basket, by having a portion of the outer basket formed from a screen or mesh, or combinations thereof. The outer basket can be made from sub-sections that are assembled inside of the reactor vessel.

A "scallop" is a conduit installed adjacent to and vertically along the inside wall of a reactor vessel. The scallops can have a semicircular cross-section or a trapezoidal cross-sectional shape. The scallops have openings that permit the passage of the feed stream, but not the passage of the catalyst particles. The passage of the feed stream can be accomplished by having slots formed into the scallop, by having a portion of the scallop formed from a screen or mesh, or combinations thereof. The scallops fit against the inside of reactor wall 120, with the slots, screen or mesh of the scallops facing the catalyst bed 130. The scallops are typically 8 to 14 inches wide, but are not limited thereto. In an embodiment, the screen can comprise welded wires and rods. In a further embodiment, the screen can comprise welded Johnson Screens® Vee-Wire® and rods. As a further refinement, slots and screens on the scallop can be oriented vertically to allow catalyst particles to move up and down during processing without becoming abraded by the screen or slot edges. During operation of the aromatization reactor vessel, the scallops can distribute the feed stream along the inside wall or collect the feed stream from the catalyst bed, depending on the direction of flow. In standard flow, the feed flows radially to the center of the reactor vessel across the catalyst bed 130. In the center of the reactor vessel is the process outlet conduit, which can be a vertical perforated pipe, also referred to as a center pipe 135.

The reactor wall 120, the center pipe 135, and other elements of the aromatization reactor vessel 110 in FIG. 1 generally can be cylindrical in shape, but other geometries and orientations can be employed. For instance, as an alternative to a circular cross-section (when viewed from above, such as from the reactor inlet 150), the center pipe can have a rectangular, elliptical, or oval cross-section. Nonetheless, in particular embodiments of this invention, the center pipe 135 and the reactor wall 120 are arranged concentrically, or the center pipe 135 and the catalyst bed 130 are arranged concentrically, or the center pipe 135, the catalyst bed 130, and the reactor wall 120 are arranged concentrically, or the center pipe 135, the catalyst bed 130, and the outer particle barrier 137 are arranged concentrically, or the center pipe 135, the catalyst bed 130, the outer particle barrier 137, and the reactor wall 120 are arranged concentrically.

The reactor wall 120, the center pipe 135, the top cover plate 138, the outer particle barrier 137, and other surfaces within the aromatization reactor vessel 110 can be constructed of any suitable metal material, the selection of which can depend upon the desired operating temperature, desired operating pressure, and inertness to the reactor contents (for example, catalyst, $H_2$, aromatic hydrocarbons, non-aromatic hydrocarbons), amongst other factors. Typical metal materials include austenitic stainless steels, including 304, 316, 321, 347, 410S, 600, or 800 stainless steel, and the like. Moreover, a coating or layer containing any suitable material, compound, alloy, or metal, such as tin, can used on any reactor surface (for example, reactor wall 120 or center pipe 135) to provide resistance to carburization and metal dusting; representative protective layer materials are disclosed in U.S. Pat. Nos. 5,866,743, 6,548,030, 8,119,203, and 9,085,736, which are incorporated herein by reference in their entirety. As indicated by the dashed lines in FIG. 1, the center pipe 135 can be porous to allow flow through it, but not so porous that catalyst particles from the catalyst bed 130 can enter the center pipe 135. Hence, the center pipe 135 can comprise screens, mesh sections, perforated metal sheets, or combinations thereof, within the reactor vessel 110. In an embodiment, the center pipe 135 can comprise welded wires and rods. In a further embodiment, the screen can comprise welded Johnson Screens® Vee-Wire® and rods. As a further refinement, slots and screens on the center pipe 135 can oriented vertically to allow catalyst particles to move up and down during processing without becoming abraded by the screen or slot edges.

The aromatization reactor vessel 110 can be configured for operating temperatures that typically fall within the 350° C. to 600° C. range. In one embodiment, the reactor vessel 110 can be configured for decreasing temperature from the outer annulus 125 to the center pipe 135, while in another embodiment, the reactor vessel 110 can be configured for decreasing temperature from the center pipe 135 to the outer annulus 125, and this can depend on the flow path (or flow direction) within the reactor vessel 110. In these and other embodiments, the reactor vessel 110 can be configured for radial flow, while not being limited thereto. For instance, traditional packed bed reactors can be employed in embodiments of this invention.

Additionally or alternatively, the reactor vessel 110 can further comprise an integrated heat exchange system around at least a portion of the reactor vessel for controlling temperature (heating or cooling) within the reactor vessel, if desired. Additional information on features and designs of aromatization reactor vessels that can be employed in the aromatization reactor vessels described herein is disclosed in U.S. Pat. Nos. 6,548,030, 7,544,335, 7,582,272, 8,119,203, and 9,085,736, which are incorporated herein by reference in their entirety.

Also included in the aromatization reactor vessel 110 of FIG. 1 is a membrane tube 140A-B positioned within the center pipe 135, and having a permeable section (140A) and impermeable section (140B), although other locations for the membrane tube are contemplated as disclosed herein. Further, more than one membrane tube 140A-B can be present in the aromatization reactor vessel 110, whether located in the center pipe 135 or elsewhere. The membrane tube is designed to remove $H_2$ from the stream within the center pipe 135, and thus the membrane tube 140A-B has an inner permeate side, and an outer process side that faces the center pipe. The $H_2$ that collects on the permeate side of the membrane tube 140A-B flows in the direction of the arrows in FIG. 1 to the membrane tube outlet 145. In an embodiment of this invention, the stream exiting the membrane tube outlet 145 can be a $H_2$ product stream having a purity of at least 95 mole % $H_2$, or at least 97 mole % $H_2$. In another embodiment, the stream exiting the membrane tube outlet 145 can be a $H_2$ recycle stream having a purity of at least 95 mole % $H_2$, or at least 97 mole % $H_2$.

Similar to the other elements of the aromatization reactor vessel 110, the membrane tube 140A-B generally can be cylindrical in shape, but other geometries and orientations can be employed, if desired. The portion of the membrane tube 140A within the center pipe 135 is depicted with dashed lines to indicate that this portion of the membrane tube is permeable to $H_2$. The portion of the membrane tube 140B that carries the $H_2$ permeate out of the reactor vessel is depicted with solid lines to indicate that this portion of the membrane tube is not permeable to $H_2$.

The membrane tube 140A-B can be constructed of any suitable material, the selection of which can depend upon the desired operating temperature, desired operating pressure, inertness to the reactor contents (for example, catalyst, $H_2$, aromatic hydrocarbons, non-aromatic hydrocarbons), and the permeability selectivity of $H_2$ (the permeate) versus other reactor contents (for example, feed stream, aromatic hydrocarbons, non-aromatic hydrocarbons), amongst other factors. The membrane tube 140A-B generally is configured for operating temperatures of at least 260° C., at least 400° C., or at least 480° C., and in some embodiments, up to an operating temperature of as much as 600° C. Likewise, the membrane tube generally is configured for operating pressures of at least 20 psig, at least 25 psig, or at least 30 psig, and in some embodiments, up to an operating pressure of as much as about 60 to about 100 psig. The membrane tube can be configured to operate at any suitable $H_2$ partial pressure gradient across the membrane tube, for example, from about 1.5:1 to about 10:1 or from about 2:1 to about 10:1, and the like. Moreover, the membrane tube can be capable of long-term continuous use under standard aromatization reaction conditions. Illustrative and non-limiting examples of materials that can be used to form the membrane tube can include, but are not limited to, a polymer, a ceramic, a molecular sieve, a metal, and the like, as well as combinations of two or more of these materials.

In an embodiment, the membrane tube 140A-B can comprise a transition metal or a transition metal alloy, in which the typical transition metal element can be nickel, platinum, or palladium, and the like, as well as combinations thereof. In another embodiment, the membrane tube can comprise palladium (for example, a palladium alloy). For instance, the membrane tube can contain sections of palladium with sections of another metal, such as stainless steel interspersed. In some embodiments, the aromatization reactor vessel can contain a membrane tube constructed of any suitable metal material comprising palladium (or a Group 10 element) and configured to selectively remove $H_2$ from the reactor vessel. In other embodiments, the membrane tube can constructed of any suitable $H_2$ permeable material, in which particles or beads, and the like, at least partially fill the membrane tube.

If desired, to minimize damage to the portion of the membrane tube 140A within the center pipe 135 resulting from reactor vessel contents and foreign debris, to increase structural integrity, to increase longevity during continuous production, or combinations thereof, the membrane tube 140A can be stabilized with a mesh on the inner permeate side of the membrane tube 140A, the membrane tube 140A can be protected or stabilized with a screen or mesh on the outer process side of the membrane tube 140A, the membrane tube 140A can be protected by one or more baffles on the outer process side of the membrane tube 140A, or combinations thereof. The mesh, screen, and baffles contemplated herein can be constructed of any suitable metal material, such as carbon steel, stainless steel, and the like, in any suitable shape. In some embodiments, the mesh, screen, or baffles can comprise a perforated metal sheet. In some embodiments, the mesh, screen, or baffles can comprise Johnson Screens® Vee-Wire®. Additionally, a coating or layer containing any suitable material, compound, alloy, or metal, such as tin, can be used on any surface of the mesh, of the screen, or of the baffles to provide resistance to carburization and metal dusting.

While not shown in FIG. 1, the reactor vessel 110 can contain braces, clamps, straps, and the like, as well as combinations thereof, as would be readily recognized by one of ordinary skill in the art, for securing the membrane tube 140A-B, the center pipe 135, the outer particle barrier 137, and other reactor internals.

Figure 2:
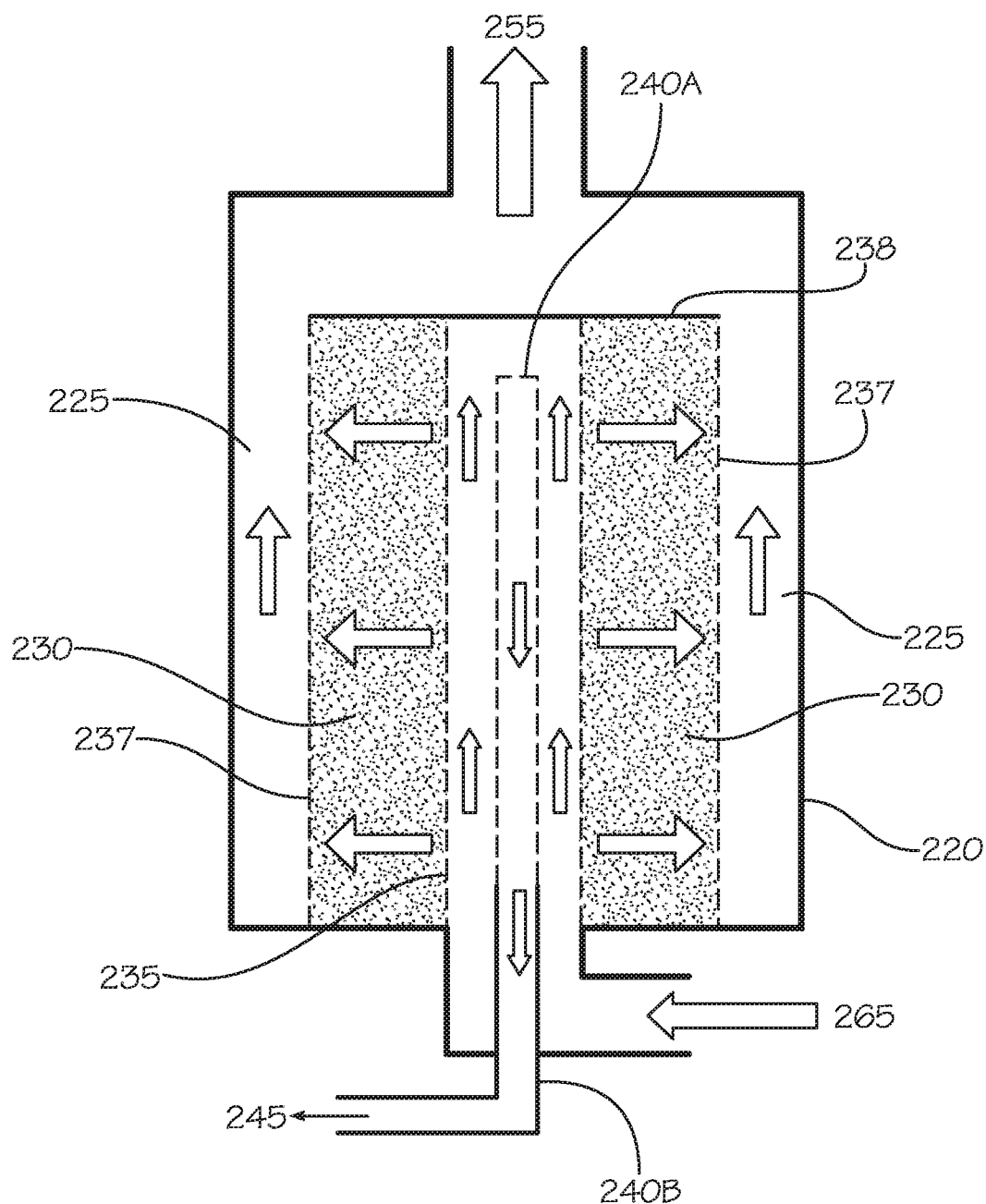
FIG. 2 illustrates a partial cross-sectional view of a reactor vessel with a membrane tube in a center pipe in another embodiment of the present invention.

Referring now to FIG. 2, another aromatization reactor vessel 210 is illustrated. Similar to FIG. 1, the aromatization reactor vessel 210 of FIG. 2 can include a reactor wall 220, a center pipe 235 surrounded by a catalyst bed 230, an outer particle barrier 237 surrounding the catalyst bed 230, and an outer annulus 225 between the outer particle barrier 237 and the reactor wall 220. This aromatization reactor vessel 210 is configured for reverse flow, and thus can include a reactor inlet 265 for a feed stream connected to the center pipe 235, a top cover plate 238, and a reactor outlet 255 for a reactor effluent, as shown in FIG. 2. The arrows in FIG. 2 illustrate a typical flow path for a feed stream (for example, effluent from another aromatization reactor vessel) entering the aromatization reactor vessel 210, for instance, starting at the reactor inlet 265, then to the center pipe 235, through the catalyst bed 230 and the outer particle barrier 237, into the outer annulus 225, and finally to the reactor outlet 255 as reactor effluent.

Also included in the aromatization reactor vessel 210 of FIG. 2 is a membrane tube 240A-B having a permeable section (240A) and an impermeable section (240B), and the membrane tube is positioned within the center pipe 235, although other locations for the membrane tube are contemplated as disclosed herein. Additionally, more than one membrane tube 240A-B can be present in the aromatization reactor vessel 210, whether located in the center pipe 235 or elsewhere. The membrane tube 240A-B is designed to remove $H_2$ from the stream within the center pipe 235, and thus the membrane tube 240A-B has an inner permeate side, and an outer process side that faces the center pipe 235. The $H_2$ that permeates through the membrane tube flows in the direction of the arrows in FIG. 2 to the membrane tube outlet 245. The portion of the membrane tube 240A within the center pipe 235 is depicted with dashed lines to indicate that this portion of the membrane tube is permeable to $H_2$. The portion of the membrane tube 240B that carries the $H_2$ permeate out of the reactor vessel is depicted with solid lines to indicate that this portion of the membrane tube is not permeable to $H_2$.

The features and characteristics of the aromatization reactor vessel 210 and the parts shown in FIG. 2 can be generally the same as the corresponding parts shown and described hereinabove in relation to FIG. 1.

Figure 3:
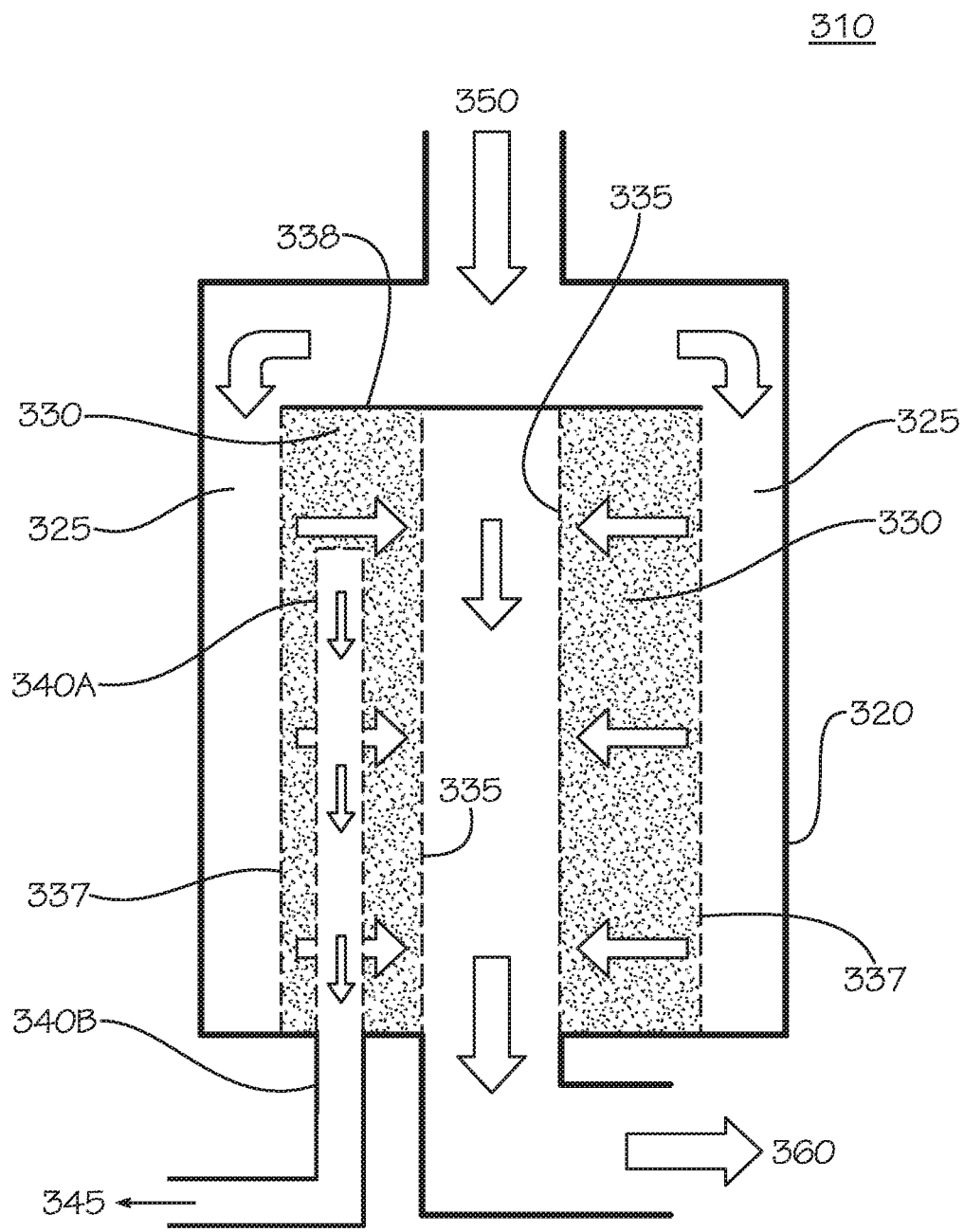
FIG. 3 illustrates a partial cross-sectional view of a reactor vessel with a membrane tube in a catalyst bed in another embodiment of the present invention.

Referring now to FIG. 3, another aromatization reactor vessel 310 is illustrated. Similar to FIG. 1, the aromatization reactor vessel 310 of FIG. 3 can include a reactor wall 320, a center pipe 335 surrounded by a catalyst bed 330, an outer particle barrier 337 surrounding the catalyst bed 330, and an outer annulus 325 between the outer particle barrier 337 and the reactor wall 320. The reactor vessel 310 can further include a reactor inlet 350 for a feed stream, a top cover plate 338, and a reactor outlet 360 connected to the center pipe 335 as shown in FIG. 3. The arrows in FIG. 3 illustrate a typical flow path for a feed stream entering the aromatization reactor vessel 310, for instance, starting at the reactor inlet 350, then directed to the outer annulus 325 by the top cover plate 338, then through the outer particle barrier 337 and the catalyst bed 330, into the center pipe 335, and finally to the reactor outlet 360 as reactor effluent. As disclosed herein, in other embodiments of this invention, the flow path (or flow direction) can be reversed, and the inlet and outlet locations can be reversed in FIG. 3 (for example, in a manner similar to FIG. 2).

Also included in the aromatization reactor vessel 310 of FIG. 3 is a membrane tube 340A-B positioned within the catalyst bed 330 and having a permeable section (340A) and impermeable section (340B), although other locations for the membrane tube are contemplated as disclosed herein. Further, more than one membrane tube 340A-B can be present in the aromatization reactor vessel 310, whether located in the catalyst bed 330 or elsewhere. Additionally, the membrane tube 340A-B can run the entire height of the catalyst bed 330, or any portion thereof; for instance, the membrane tube 340A-B in FIG. 3 extends about 75% of the full height of the catalyst bed.

The membrane tube 340A-B is designed to remove $H_2$ from the stream within the catalyst bed 330, and thus the membrane tube 340A-B has an inner permeate side, and an outer process side that faces the catalyst bed. The $H_2$ that permeates through the membrane tube flows in the direction of the arrows in FIG. 3 to the membrane tube outlet 345. The portion of the membrane tube 340A within the catalyst bed 330 is depicted with dashed lines to indicate that this portion of the membrane tube is permeable to $H_2$. The portion of the membrane tube 340B that carries the $H_2$ permeate out of the reactor vessel is depicted with solid lines to indicate that this portion of the membrane tube is not permeable to $H_2$.

The features and characteristics of the aromatization reactor vessel 310 and the parts shown in FIG. 3 can be generally the same as the corresponding parts shown and described hereinabove in relation to FIG. 1.

Figure 4:
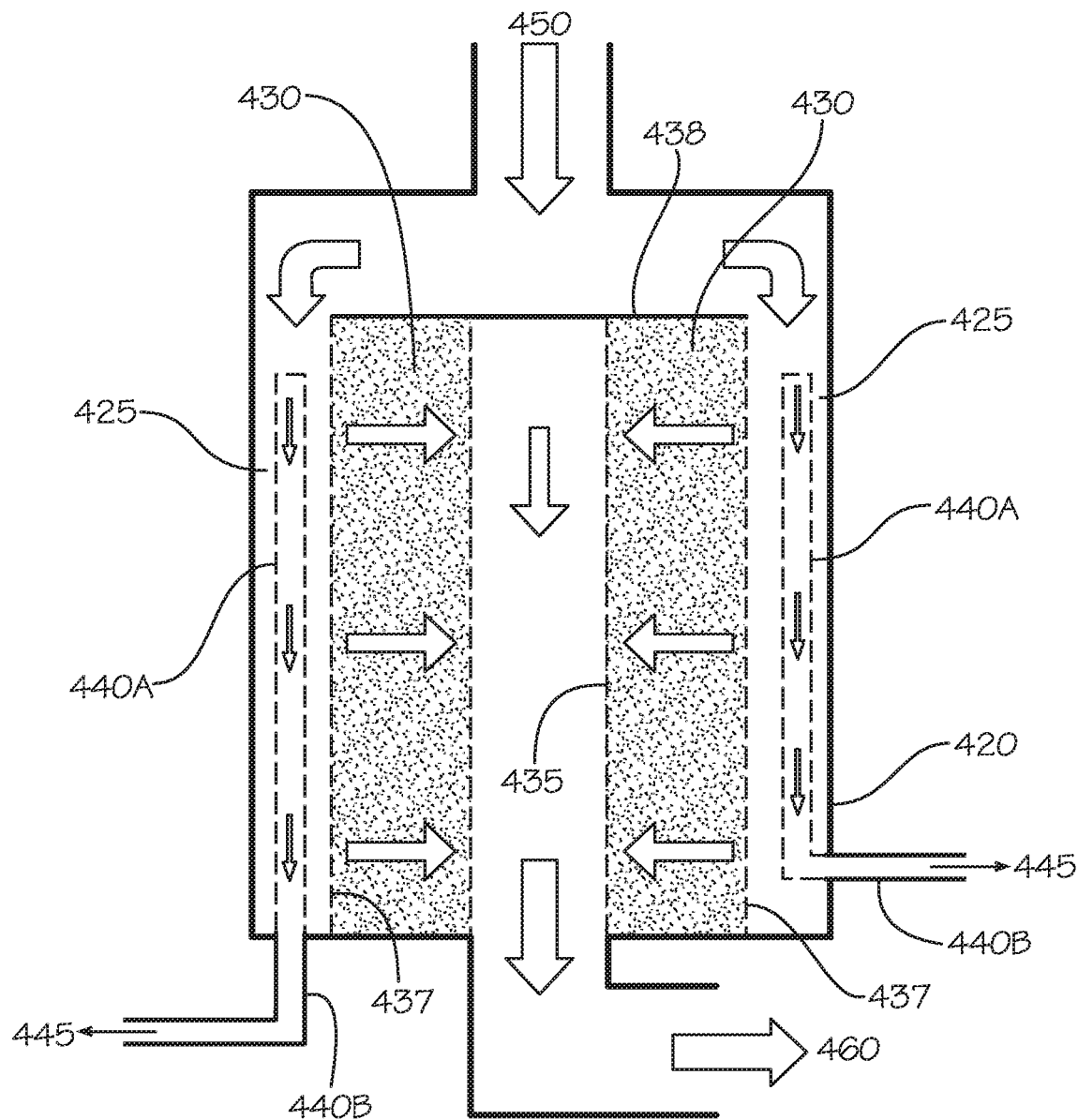
FIG. 4 illustrates a partial cross-sectional view of a reactor vessel with a membrane tube in an outer annulus in another embodiment of the present invention.

Referring now to FIG. 4, another aromatization reactor vessel 410 is illustrated. Similar to FIG. 1, the aromatization reactor vessel 410 of FIG. 4 can include a reactor wall 420, a center pipe 435 surrounded by a catalyst bed 430, an outer particle barrier 437 surrounding the catalyst bed 430, and an outer annulus 425 between the outer particle barrier 437 and the reactor wall 420. The reactor vessel 410 can further include a reactor inlet 450 for a feed stream, a top cover plate 438, and a reactor outlet 460 through which flows a reactor effluent stream. The reactor outlet 460 is connected to the center pipe 435 as shown in FIG. 4. The arrows in FIG. 4 illustrate a typical flow path for a feed stream entering the aromatization reactor vessel 410, for instance, starting at the reactor inlet 450, then to the outer annulus 425, through the outer particle barrier 437 and the catalyst bed 430, into the center pipe 435, and finally to the reactor outlet 460. As disclosed herein, in other embodiments of this invention, the flow path (or flow direction) can be reversed, and the inlet and outlet locations can be reversed in FIG. 4 (for example, in a manner similar to FIG. 2).

Also included in the aromatization reactor vessel 410 of FIG. 4 are membrane tubes 440A-B, each having a permeable section (440A) and impermeable section (440B), positioned within the outer annulus 425, although other locations for the membrane tube are contemplated as disclosed herein. The membrane tubes 440A-B can run the entire height of the outer annulus 425, or any portion thereof. Moreover, the membrane tubes 440A-B can exit the reactor vessel 410 at any suitable location, such as at the bottom or at the side of the reactor vessel 410, as shown in FIG. 4.

The membrane tubes 440A-B are designed to remove $H_2$ from the stream within the outer annulus 425, and thus the membrane tubes 440A-B have an inner permeate side, and an outer process side that faces the outer annulus. The $H_2$ that permeates through the membrane tubes 440A-B flows in the direction of the arrows in FIG. 4 to the membrane tube outlets 445. The portions of the membrane tubes 440A within the outer annulus 425 are depicted with dashed lines to indicate that these portions of the membrane tube is permeable to $H_2$. The portions of the membrane tubes 440B that carry the $H_2$ permeate out of the reactor vessel are depicted with solid lines to indicate that these portions of the membrane tube are not permeable to $H_2$.

The features and characteristics of the aromatization reactor vessel 410 and the parts shown in FIG. 4 can be generally the same as the corresponding parts shown and described hereinabove in relation to FIG. 1.

While not shown in FIG. 4, and as described hereinabove in relation to FIG. 1, the outer annulus 425 in the aromatization reactor vessel 410 can contain scallops, and in an embodiment of this invention, a scallop (one or more) can be replaced with a membrane tube 440A-B. Alternatively, the outer annulus 425 in the aromatization reactor vessel 410 can contain scallops, and a membrane tube (one or more) can be positioned within (or inside) a scallop (one or more). The scallops can be of any suitable design or configurations, such as trapezoidal or semi-circular. Additional information on scallop features of aromatization reactor vessels that can be employed in the aromatization reactor vessels described herein are disclosed in U.S. Pat. Nos. 5,366,704, 6,224,838, 7,544,335, and 8,119,203, which are incorporated herein by reference in their entirety.

Figure 5:
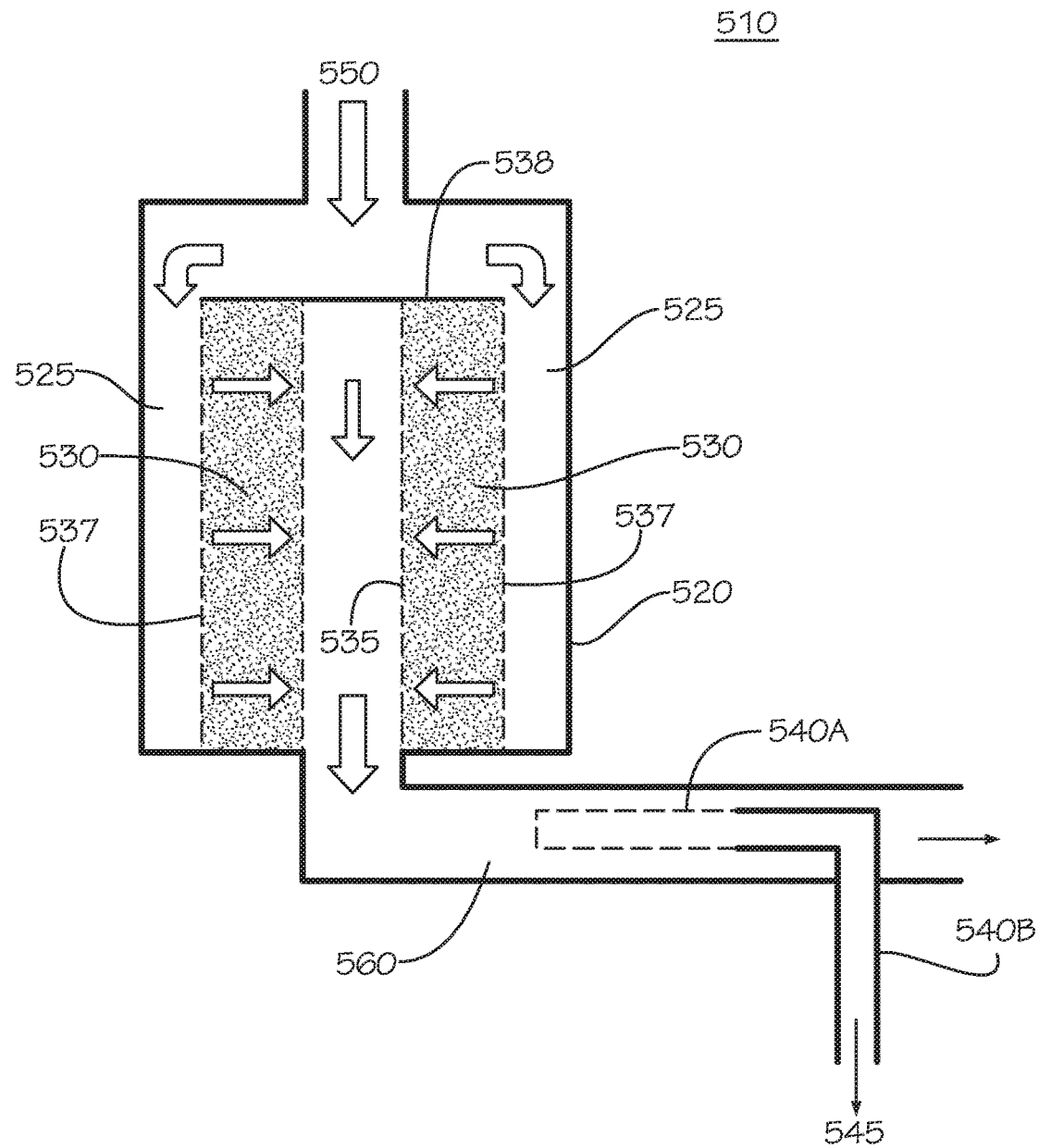
FIG. 5 illustrates a partial cross-sectional view of a reactor vessel with a membrane tube in a reactor outlet in another embodiment of the present invention.

Referring now to FIG. 5, another aromatization reactor vessel 510 is illustrated. Similar to FIG. 1, the aromatization reactor vessel 510 of FIG. 5 can include a reactor wall 520, a center pipe 535 surrounded by a catalyst bed 530, an outer particle barrier 537 surrounding the catalyst bed 530, and an outer annulus 525 between the outer particle barrier 537 and the reactor wall 520. The reactor vessel 510 can further include a reactor inlet 550 for a feed stream, a top cover plate 538, and a reactor outlet 560 through which flows a reactor effluent stream. The reactor outlet 560 is connected to the center pipe 535 as shown in FIG. 5. The arrows in FIG. 5 illustrate a typical flow path for a feed stream entering the aromatization reactor vessel 510, for instance, starting at the reactor inlet 550, then directed to the outer annulus 525 by the top cover plate 538, then through outer particle barrier 537 and the catalyst bed 530, into the center pipe 535, then to the reactor outlet 560 as reactor effluent. As disclosed herein, in other embodiments of this invention, the flow path (or flow direction) can be reversed, and the inlet and outlet locations can be reversed in FIG. 5 (for example, in a manner similar to FIG. 2).

Also included in the aromatization reactor vessel 510 of FIG. 5 is a membrane tube 540A-B having a permeable section (540A) and an impermeable section (540B), and positioned within the reactor outlet 560, although other locations for the membrane tube are contemplated as disclosed herein. Further, more than one membrane tube 540A-B can be present in the aromatization reactor vessel 510, whether located in the reactor outlet 560 or elsewhere. The membrane tube 540A-B is designed to remove $H_2$ from the reactor effluent stream in the reactor outlet 560, and thus the membrane tube 540A-B has an inner permeate side, and an outer process side that faces the reactor outlet. The $H_2$ that permeates through the membrane tube flows in the direction of the arrow in FIG. 5 to the membrane tube outlet 545. A portion of the membrane tube 540A within the reactor outlet 560 is depicted with dashed lines to indicate that this portion of the membrane tube is permeable to $H_2$. The portion of the membrane tube 540B that carries the $H_2$ permeate out of the reactor outlet is depicted with solid lines to indicate that this portion of the membrane tube is not permeable to $H_2$.

The features and characteristics of the aromatization reactor vessel 510 and the parts shown in FIG. 5 can be generally the same as the corresponding parts shown and described hereinabove in relation to FIG. 1.

Also encompassed herein are aromatization reactor vessel systems, and such systems generally can comprise two or more aromatization reactor vessels in series, at least one of which is any of the aromatization reactor vessels described hereinabove (i.e., containing a membrane tube). For example, an exemplary reactor system can comprise any suitable number of reactor vessels in series, such as from 2 to 8 vessels, from 2 to 7 vessels, from 3 to 8 vessels, from 4 to 7 vessels, 5 vessels, 6 vessels, 7 vessels, or 8 vessels, in series. The reactor system can either be configured for a single pass of the non-aromatic hydrocarbon through the series of reactor vessels, or the reactor system can be configured to separate the unreacted non-aromatic hydrocarbons from the aromatic hydrocarbons, with subsequent recycling of the unreacted non-aromatic hydrocarbons to the first reactor vessel in the series.

In the series of reactor vessels, the specific vessel (or vessels) containing the membrane tube (or tubes) is not particularly limited. Generally, however, the reactor vessel containing the membrane tube can be the second, third, fourth, or fifth vessel in the series, or the third or fourth vessel in the series. Additionally, more than reactor vessel containing a membrane tube can be present in the aromatization reactor vessel system.

In one embodiment, the reactor vessel containing the membrane tube can have an amount of catalyst that is less than the amount of catalyst in the next reactor vessel in the series, while in another embodiment, the reactor vessel containing the membrane tube can have an amount of catalyst that is equal to the amount of catalyst in the next reactor vessel in the series. Additionally or alternatively, the total amount of the catalyst in the aromatization reactor vessel containing the membrane tube and each preceding reactor vessel in the series can be in a range from about 10 to about 60 wt. %, from about 15 to about 50 wt. %, or from about 20 to about 45 wt. %, based on the sum of the catalyst contained in all of the reactor vessels in the system.

The aromatization reactor vessel system can further comprise a furnace before any or each reactor vessel in the series, and the furnace can be capable of heating any feed stream to a reactor vessel operating temperature of from about 350° C. to about 600° C. Typically, the reactor vessel system contains a furnace before the first reactor vessel in the series. Also typically, the reactor vessel system contains a furnace before each reactor vessel in the series. Each furnace can be configured to heat a reactor effluent of the previous reactor vessel in the series to a temperature of from about 350° C. to about 600° C. before entering the next vessel in the series.

The $H_2$-containing stream that exits the membrane tube outlet can have a purity of at least 95 mole % $H_2$, or at least 97 mole % $H_2$, and can be used as a component of a feed stream to another reactor vessel in the series (for example, the first reactor). Alternatively, the $H_2$-containing stream having a purity of at least 95 mole % $H_2$, or at least 97 mole % $H_2$, can be a product stream. Alternatively, the $H_2$-containing stream having a purity of at least 95 mole % $H_2$, or at least 97 mole % $H_2$, can be a reacted with benzene in a cyclohexane production process. Alternatively, the $H_2$-containing stream having a purity of at least 95 mole % $H_2$, or at least 97 mole % $H_2$, can be reacted with any suitable hydrocarbon (for example, removal of sulfur or nitrogen from refinery streams by hydrotreating), or can be used in any suitable chemical process that requires $H_2$. Other uses for the $H_2$ from the membrane tube outlet stream are readily apparent to one of skill in the art.

In another embodiment, an aromatization reactor vessel system is provided, and in this embodiment, the system can comprise a series of two or more furnace-reactor pairs, each pair connected by a transfer pipe, wherein a membrane tube configured to remove $H_2$ is positioned in at least one transfer pipe, and wherein the membrane tube has an inner permeate side and an outer process side, the outer process side facing the transfer pipe. In this embodiment, the features and characteristics of the reactor vessel and the membrane tube can be equivalent to that of any reactor vessel and any membrane tube described herein.

In accordance with other embodiments of this invention, aromatization reactor vessel systems can comprise an aromatization reactor vessel (for example, as described in reference to FIGS. 1-5, with or without a membrane tube) and a $H_2$ removal system configured to remove $H_2$ from a reactor effluent, wherein the $H_2$ removal system generally is positioned downstream of the reactor outlet. In an embodiment directed to conventional flow, the aromatization reactor vessel can comprise a reactor wall, a catalyst bed and an outer particle barrier positioned within the reactor vessel, an outer annulus positioned between the reactor wall and the outer particle barrier, the outer annulus and the outer particle barrier surrounding the catalyst bed, a reactor inlet for a feed stream, and a reactor outlet connected to a center pipe, the center pipe positioned in the reactor vessel and surrounded by the catalyst bed. The flow path for the feed stream can begin at the reactor inlet, then directed to the outer annulus by the top cover plate, through the outer particle barrier and the catalyst bed, into the center pipe, and to the reactor outlet. Alternatively, in an embodiment directed to reverse flow, the aromatization reactor vessel can comprise a reactor wall, a catalyst bed positioned within the reactor vessel, an outer annulus positioned between the reactor wall and an outer particle barrier, the outer particle barrier and the outer annulus surrounding the catalyst bed, a reactor inlet for a feed stream and connected to a center pipe, the center pipe positioned in the reactor vessel and surrounded by the catalyst bed and outer particle barrier, and a reactor outlet connected to the outer annulus. The flow path for the feed stream can begin at the reactor inlet, continue to the center pipe, proceed through the catalyst bed and the outer particle barrier, into the outer annulus, and to the reactor outlet.

Regardless of direction of flow, the aromatization reactor vessel system can comprise a $H_2$ removal system configured to remove $H_2$ from the reactor effluent, and the $H_2$ removal system generally is positioned well downstream of the reactor outlet. The $H_2$ removal system can comprise a shell containing a membrane tube such that the reactor effluent passes through the shell, and the membrane tube can have an inner permeate side and an outer process side, wherein the outer process side faces the shell.

Figure 6A:
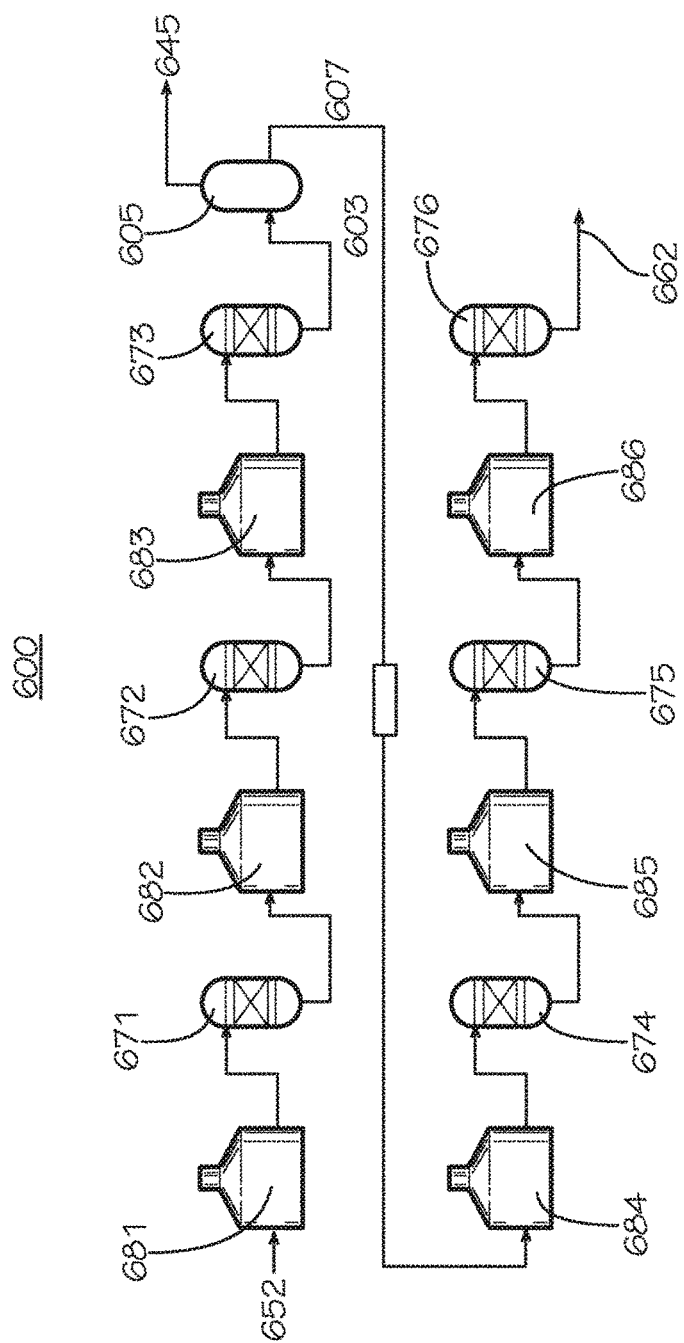
FIG. 6A illustrates a reactor system containing a series of furnaces and reactor vessels, and a hydrogen removal system, in another embodiment of the present invention.
Figure 6B:
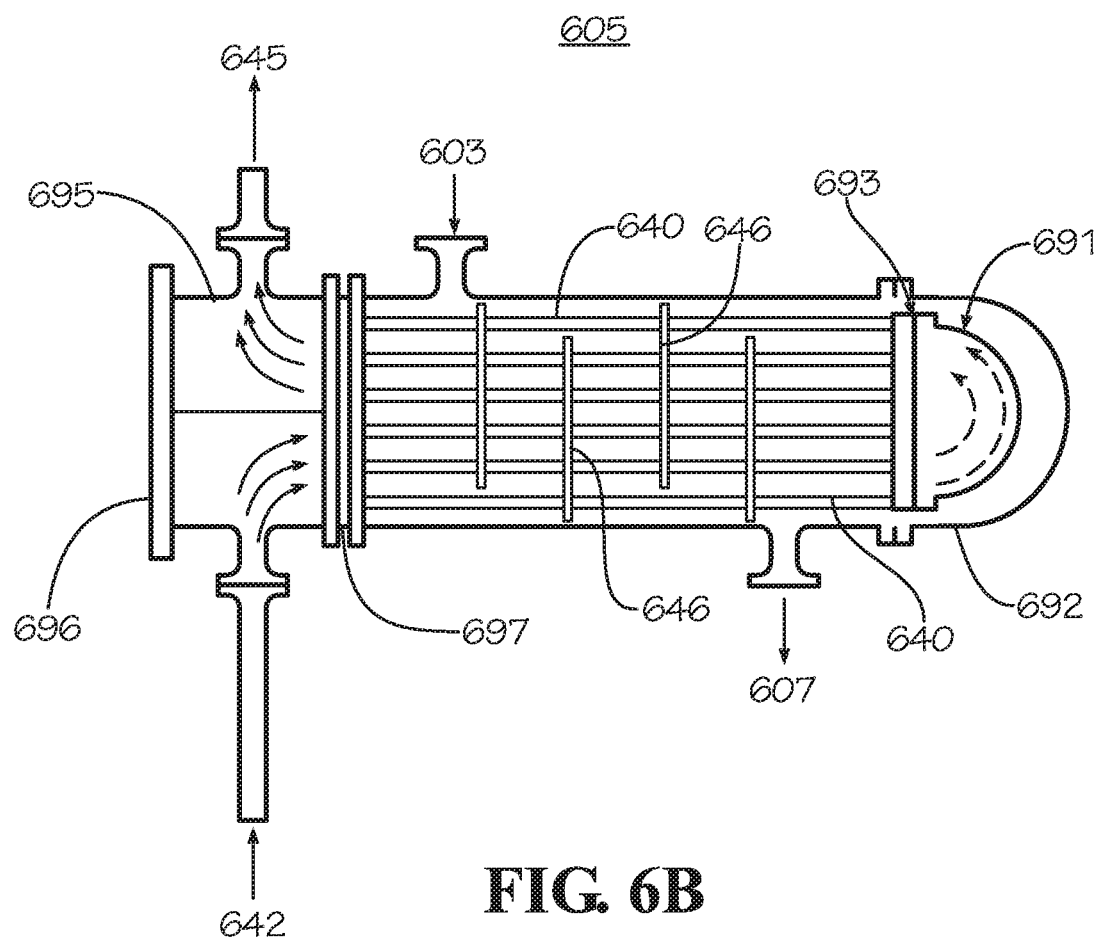
FIG. 6B illustrates a partial cross-sectional view of a hydrogen removal system that can be used in the system of FIG. 6A.

FIGS. 6A-6B present an illustrative example of an aromatization reactor vessel system 600 comprising an aromatization reactor vessel and a $H_2$ removal system 605. In FIG. 6A, six reactor vessels 671, 672, 673, 674, 675, 676 are shown in series, with a corresponding furnace 681, 682, 683, 684, 685, 686 preceding each respective reactor vessel in the system 600. The furnaces 681, 682, 683, 684, 685, 686 in FIG. 6A can be capable of heating or reheating any feed stream or reactor effluent to a reactor vessel operating temperature of from about 350° C. to about 600° C. A feed stream 652 enters the first furnace 681 and then the first reactor vessel 671. Each reactor vessel can be configured to contact the feed stream with an aromatization catalyst to catalytically convert at least a portion of the non-aromatic hydrocarbon to produce an aromatic hydrocarbon (for example, benzene, toluene, xylenes, and the like, as well as combinations thereof) and $H_2$. Progressively more of the non-aromatic hydrocarbon is converted to the aromatic hydrocarbon, starting with the more easily converted non-aromatic hydrocarbons, as each reactor vessel in the series has been traversed. A final reactor effluent 662 exits the last reactor vessel 676 in the system 600.

The $H_2$ removal system 605 can be placed at any suitable location in the system 600 and series of reactor vessels, and more than one $H_2$ removal system can be used, although FIG. 6A shows a single $H_2$ removal system 605 between reactor vessel 673 and reactor vessel 674 (and furnace 684). The $H_2$ removal system 605 can be configured to remove $H_2$ produced in the reactor vessel system 600 as the conversion of the non-aromatic hydrocarbon to the aromatic hydrocarbon increases. The reactor effluent 603 from reactor vessel 673 enters the $H_2$ removal system 605 and the exiting reactor effluent 607 leaves the $H_2$ removal system and proceeds to the next furnace 684 and reactor vessel 674 in the series. The amount (i.e., concentration) of $H_2$ in the exiting reactor effluent 607 is less than that in the inlet reactor effluent 603. The $H_2$ that is removed exits the $H_2$ removal system 605 via the $H_2$ exit port 645 with a typical purity of at least 95 mole % $H_2$, or at least 97 mole % $H_2$, in some embodiments.

The aromatization reactor vessel system 600 shown in FIG. 6A contains six reactor vessels in series, although any suitable number of reactor vessels in series can be used (with at least one $H_2$ removal system positioned between any two of the reactor vessels), such as, for example, from 2 to 8 reactor vessels, from 2 to 7 reactor vessels, from 3 to 8 reactor vessels, from 4 to 7 reactor vessels, 5 reactor vessels, 6 reactor vessels, 7 reactor vessels, or 8 rector vessels. While not limited thereto, the $H_2$ removal system can be located after the second, third, fourth, fifth, sixth, or seventh vessel in the series, or after the third or fourth vessel in the series. Additionally, more than one $H_2$ removal system can be present in the aromatization reactor vessel system. The reactor system can either be configured for a single pass of the non-aromatic hydrocarbon through the series of reactor vessels, or the reactor system can be configured to separate the unreacted non-aromatic hydrocarbons from the aromatic hydrocarbons, with subsequent recycling of the unreacted non-aromatic hydrocarbons to the first reactor vessel in the series.

In one embodiment, the reactor vessel before the $H_2$ removal system (reactor vessel 673 in FIG. 6A) can have an amount of catalyst that is less than the amount of catalyst in the next reactor vessel in the series (reactor vessel 674), while in another embodiment, the reactor vessel before the $H_2$ removal system can have an amount of catalyst that is more than the amount of catalyst in the next reactor vessel in the series. Additionally or alternatively, the total amount of the catalyst in the reactor vessels before the $H_2$ removal system can be in a range from about 10 to about 60 wt. %, from about 15 to about 50 wt. %, or from about 20 to about 45 wt. %, based on the sum of the catalyst contained in all of the reactor vessels in the system.

FIG. 6B shows a partial cross-sectional view of one embodiment of the hydrogen removal system 605 that can be used in the aromatization reactor vessel system of FIG. 6A, with the inlet reactor effluent 603, the exiting reactor effluent 607, and the $H_2$ exit port 645 labeled accordingly. The design of the hydrogen removal system 605 is similar to that of a shell/tube heat exchanger, although other designs and configurations are possible. A plurality of membrane tubes 640 (with support baffles 646) remove $H_2$ from the aromatic stream and exit collectively through the $H_2$ exit port 645. FIG. 6B illustrates a common exit port 645 for the membrane tubes 640, although multiple exit ports for $H_2$ for the plurality of membrane tubes can be used. A pressure regulation system can be used to alter the pressure on the permeate side of the membrane tube and thus the pressure difference across the membrane tube ($\Delta P$ from the process side to permeate side of the membrane tube). An inlet stream 642 is shown, but this feature is optional. The inlet stream 642 can be employed to purge the system with inert gas prior to or after maintenance, to purge the system with hydrogen prior to or after operation, or to introduce a gas (for example, an inert gas or hydrocarbon) to lower the hydrogen partial pressure by dilution. FIG. 6B illustrates a channel head 695, channel head cover 696, and channel head tubesheet 697 of the $H_2$ removal system 605, as well as the floating head assembly—a floating head 691, a floating head cover 692, and a floating heat tubesheet 693—of the $H_2$ removal system 605.

Inside the $H_2$ removal system 605 of FIG. 6B are a plurality of membrane tubes 640 that are spaced apart from one another, although any number of membrane tubes and any configuration within the $H_2$ removal system 605 can be employed. For instance, the membrane tubes 640 can be aligned longitudinally (as shown in the FIG. 6B) in some embodiments, while the membrane tubes can be aligned transversely in other embodiments (the support baffles 646 are configured transversely in FIG. 6B). The support baffles 646 can serve the dual functions of stabilizing the membrane tubes 640 and disturbing the flow path of the reactor effluent, the latter with the objective to increase the amount of contact between the reactor effluent and the membrane tubes 640 to increase the efficiency of $H_2$ removal. If desired, additional flow-affecting elements (or baffles) can be used to further increase the contact between the reactor effluent and the membrane tubes 640, such as to promote turbulent flow within the $H_2$ removal system 605.

In another embodiment, an aromatization reactor vessel system is provided, and in this embodiment, the system can comprise a series of two or more furnace-reactor pairs, each pair connected by a transfer pipe, wherein a $H_2$ removal system configured to remove $H_2$ is connected to at least one transfer pipe, and wherein the $H_2$ removal system comprises a shell containing a membrane tube, the membrane tube having an inner permeate side and an outer process side, the outer process side facing the shell. In this embodiment, the features and characteristics of the reactor vessel, the $H_2$ removal system, and the membrane tube can be equivalent to that of any reactor vessel, $H_2$ removal system, and membrane tube described herein.

Disclosed herein are various aromatization reactor vessel systems, related reactor vessels, and integrated membrane tubes, and representative designs and configurations for these systems, vessels, and tubes. In addition, other designs and configurations are possible. For instance, in one embodiment, the membrane tube can contain an electrical system for inducing an electrical bias across the membrane tube to control a $H_2$ removal rate, such as to increase the H2 transport through the membrane tube. While not wishing to be bound by the following theory, it is believed that inducing an electrical bias can aid in atomic diffusion, thereby increasing the rate of $H_2$ diffusion beyond that achieved with only molecular $H_2$ diffusion. Regardless of the actual mechanism involved, the use of an electrical system and an electrical bias can increase the overall effectiveness of the membrane tube.

In another embodiment, the aromatization reactor vessel or system can have a hydrocarbon analyzer on the permeate side to detect leaks in the membrane tube, or to detect a higher than normal percentage of hydrocarbons in either the $H_2$-containing stream that exits the membrane tube or within the membrane tube itself. In yet another embodiment, the reactor vessel or system can contain a $H_2$-containing stream pressure control system (for example, a backpressure regulator, a valve, or a flow controller, among others) for controlling the $H_2$ partial pressure on the permeate side of the membrane tube, thus controlling the $H_2$ partial pressure on the process side of the membrane tube. For instance, the $H_2$ exit port 645 in FIGS. 6A-6B can have a pressure control system, such as a backpressure regulator or a flow controller.

In still another embodiment, the vessel or system can have a membrane bypass, the purpose of which can be to continue to operate the vessel or system if the membrane tube is damaged, leaking, or otherwise needs to be bypassed. In still another embodiment, there could be two or more parallel membrane tubes or $H_2$ removal systems, one in service and the others on standby, analogously to how many filter systems are used in continuous production. This can be beneficial in circumstances where the membrane tube has a different longevity or useful life than that of the catalyst bed, such that a bypass or swap between parallel membrane tubes or $H_2$ removal systems would increase the overall production time.

Aromatization Processes

Embodiments of this invention also are directed to aromatization processes. Such processes can comprise, consist essentially of, or consist of (i) introducing a feed stream comprising $H_2$ and a non-aromatic hydrocarbon into the reactor inlet and the flow path of the any of the reactor vessels or systems disclosed herein; (ii) contacting the feed stream with an aromatization catalyst (in the catalyst bed); (iii) catalytically converting at least a portion of the non-aromatic hydrocarbon within the reactor vessel to produce an aromatic hydrocarbon and $H_2$; (iv) discharging a reactor effluent comprising the aromatic hydrocarbon from the reactor vessel via the reactor outlet; and (v) removing a portion of the $H_2$ (from the reactor vessel, from the reactor outlet, or from the reactor effluent) via the membrane tube to reduce a partial pressure of $H_2$ in the process. Beneficially, the $H_2$:hydrocarbon ratio can be reduced from about 4:1-5:1 to about 1.5:1-2:1. Generally, the features of these processes (for example, the non-aromatic hydrocarbon, the aromatization catalyst, the aromatic hydrocarbon, the amount of $H_2$ in the process and the amount removed via the membrane tube, among others) are independently described herein and these features can be combined in any combination to further describe the disclosed aromatization processes. Moreover, other process steps can be conducted before, during, or after (or any combination thereof) the steps listed in the disclosed processes, unless stated otherwise.

Consistent with embodiments disclosed herein, the aromatization catalyst can comprise a metal (for example, a Group 7-11 transition metal, a Group 14 metal) deposited on an inorganic support. The inorganic support typically can comprise an inorganic oxide, examples of which can include, but are not limited to, bound medium or large pore zeolites (crystalline aluminosilicates), amorphous inorganic oxides, as well as mixtures thereof. Large pore zeolites often can have average pore diameters in a range of from about 7 Å to about 12 Å, and non-limiting examples of large pore zeolites include L-zeolite, Y-zeolite, mordenite, omega zeolite, beta zeolite, and the like. Medium pore zeolites often can have average pore diameters in a range of from about 5 Å to about 7 Å. Amorphous inorganic oxides can include, but are not limited to, aluminum oxide, silicon oxide, titania, and combinations thereof.

The term "zeolite" generally refers to a particular group of hydrated, crystalline aluminosilicates. These zeolites exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms can be equal to 2. The framework exhibits a negative electrovalence that typically can be balanced by the inclusion of cations within the crystal, such as metals, alkali metals, alkaline earth metals, hydrogen, or combinations thereof.

In some embodiments, the inorganic support can comprise an L-type zeolite. L-type zeolite supports are a subgroup of zeolitic supports, which can contain mole ratios of oxides in accordance with the formula: $M_{2/n}OAl_2O_3xSiO_2yH_2O$. In this formula, "M" designates an exchangeable cation (one or more) such as barium, calcium, cerium, lithium, magnesium, potassium, sodium, strontium, zinc, or combinations thereof as well as non-metallic cations like hydronium and ammonium ions, which can be replaced by other exchangeable cations without causing a substantial alteration of the basic crystal structure of the L-type zeolite. The "n" in the formula represents the valence of "M"; "x" is 2 or greater; and "y" is the number of water molecules contained in the channels or interconnected voids of the zeolite.

In one embodiment, the inorganic support can comprise a bound potassium L-type zeolite, also referred to as a KL-zeolite, while in another embodiment, the inorganic support can comprise a barium ion-exchanged L-zeolite. As used herein, the term "KL-zeolite" refers to L-type zeolites in which the principal cation M incorporated in the zeolite is potassium. A KL-zeolite can be cation-exchanged (for example, with barium) or impregnated with a transition metal and one or more halides to produce a transition metal impregnated, halided zeolite or a KL supported transition metal-halide zeolite catalyst.

In the aromatization catalyst, the zeolite can be bound with a support matrix (or binder), non-limiting examples of which can include silica, alumina, magnesia, boria, titania, zirconia, various clays, and the like, including mixed oxides thereof, as well as mixtures thereof. For example, the aromatization catalyst can comprise a support matrix comprising alumina, silica, a mixed oxide thereof, or a mixture thereof. The zeolite can be bound with the support matrix using any method known in the art.

While not being limited thereto, the aromatization catalyst can comprise from about 5 wt. % to about 35 wt. % support matrix. For example, the catalyst can comprise from about 5 wt. % to about 30 wt. %, or from about 10 wt. % to about 30 wt. % support matrix. These weight percentages are based on the total weight of the aromatization catalyst.

In some embodiments, the aromatization catalyst can comprise a Group 14 metal such as tin, while in other embodiments, the aromatization catalyst can comprise a transition metal, and non-limiting examples of suitable transition metals can include iron, cobalt, nickel, ruthenium, rhodium, palladium, osmium, iridium, rhenium, platinum, gold, silver, copper, and the like, or a combination of two or more transition metals. In one embodiment, the transition metal can comprise a Group 7-11 transition metal (for example, one or more of platinum, rhenium, and gold), and in another embodiment, the transition metal can comprise a Group 10 transition metal, while in yet another embodiment, the transition metal can comprise platinum (Pt).

Typically, the aromatization catalyst can comprise from about 0.1 wt. % to about 10 wt. % metal. In another embodiment, the aromatization catalyst can comprise from about 0.3 wt. % to about 5 wt. % metal. In yet another embodiment, the aromatization catalyst can comprise from about 0.3 wt. % to about 3 wt. % metal, or from about 0.5 wt. % to about 2 wt. % metal. These weight percentages are based on the total weight of the aromatization catalyst. In circumstances where the metal comprises platinum, the aromatization catalyst can comprise from about 0.1 wt. % to about 10 wt. % platinum; alternatively, from about 0.3 wt. % to about 5 wt. % platinum; alternatively, from about 0.3 wt. % to about 3 wt. % platinum; or alternatively, from about 0.5 wt. % to about 2 wt. % platinum. In a particular embodiment contemplated herein, the aromatization catalyst can comprise platinum on a KL-zeolite.

In an embodiment, the aromatization catalyst can further comprise a halogen, such as chlorine, fluorine, bromine, iodine, or a combination of two or more halogens. For example, the aromatization catalyst can comprise chlorine, or fluorine, or both chlorine and fluorine. Chlorine can be present in the aromatization catalyst in an amount of from about 0.025 wt. % to about 5 wt. %, from about 0.025 wt. % to about 3 wt. %, or from about 0.05 wt. % to about 2 wt. %. Likewise, the aromatization catalyst can comprise from about 0.025 wt. % to about 5 wt. % fluorine, from about 0.025 wt. % to about 3 wt. % fluorine, or from about 0.05 wt. % to about 2 wt. % fluorine. These weight percentages are based on the total weight of the aromatization catalyst. In certain embodiments, the catalyst comprises chlorine and fluorine, and typically, the molar ratio of chlorine:fluorine can be in the range of from about 0.5:1 to about 4:1. Other suitable molar ratios of Cl:F can include the following non-limiting ranges: from about 1:1 to about 4:1, from about 0.5:1 to about 3:1, from about 1:1 to about 3:1, from about 0.5:1 to about 2:1, or from about 1:1 to about 2.5:1.

Examples of representative and non-limiting catalysts that are encompassed herein include those disclosed in U.S. Pat. Nos. 5,196,631, 6,190,539, 6,406,614, 6,518,470, 6,812,180, 7,153,801, and 7,932,425, the disclosures of which are incorporated herein by reference in their entirety.

Aromatization processes consistent with this invention can comprise (or consist essentially of, or consist of) the steps of (i) introducing a feed stream comprising $H_2$ and a non-aromatic hydrocarbon into the reactor inlet and the flow path of the any of the reactor vessels or systems disclosed herein; (ii) contacting the feed stream with any aromatization catalyst disclosed herein (in the catalyst bed); (iii) catalytically converting at least a portion of the non-aromatic hydrocarbon within the reactor vessel to produce an aromatic hydrocarbon and $H_2$; (iv) discharging a reactor effluent comprising the aromatic hydrocarbon from the reactor vessel via the reactor outlet; and (v) removing a portion of the $H_2$ (from the reactor vessel, from the reactor outlet, or from the reactor effluent) via the membrane tube to reduce a partial pressure of $H_2$ in the process. Suitable non-aromatic hydrocarbons, aromatic hydrocarbons, and aromatization reaction conditions for catalytically converting non-aromatic hydrocarbons to aromatic hydrocarbons are well known to those of skill in the art and are described, for example, in U.S. Pat. Nos. 4,456,527, 5,389,235, 5,401,386, 5,401,365, 6,207,042, 7,932,425, and 9,085,736, the disclosures of which are incorporated herein by reference in their entirety.

While not being limited thereto, representative aromatization reaction conditions include a reaction temperature in a range from about 350° C. to about 600° C., or about from 400° C. to about 550° C., and a reaction pressure in a range from about 20 to about 100 psig, or from about 25 to about 75 psig. Typical molar conversions of the non-aromatic hydrocarbon to the aromatic hydrocarbon in an aromatization reactor can range from about 10 to about 95%, from about 50 to about 90%, or from about 70 to about 85%.

Often, in the processes, reactor vessels, and reactor systems disclosed herein, the molar ratio of $H_2$:hydrocarbon can be relatively high, such as greater than 3:1, greater than 3.5:1, or in the range of about 2.5:1 to about 6:1, about 3:1 to about 6:1, about 3:1 to about 5:1, or about 4:1 to about 5:1, and this can adversely affect the conversion of the non-aromatic hydrocarbon to the aromatic hydrocarbon, and the selectivity and yield to desired aromatic products, such as benzene, toluene, xylenes, or combinations thereof. Beneficially, the use of the membrane tube can reduce the amount of $H_2$ (the partial pressure) such that the $H_2$:hydrocarbon molar ratio can be decreased to within a range of from about 1:1 to about 2:1, from about 1.25:1 to about 2.25:1, from about 1:1 to about 1.9:1, from about 1.5:1 to about 2:1, or from about 1.25:1 to about 1.75:1. In this ratio of $H_2$:hydrocarbon, the "hydrocarbon" includes both aromatic hydrocarbons and non-aromatic hydrocarbons, but excludes cracked products of lower carbon numbers ($C_1$-$C_4$).

In some embodiments, this hydrogen removal can result in increases in the molar conversion of the non-aromatic hydrocarbon to the aromatic hydrocarbon of at least 2%, at least 4%, or at least 6%, and often up to 8-12%, when compared to the same process, vessel, or system without the membrane tube (for example, with the membrane tube disabled). This effect of hydrogen removal can be particularly beneficial as conversion levels increase, such as in the last few reactors in a series of reactors in an aromatization reactor vessel system, where the removal of $H_2$ can improve the thermodynamic equilibrium for the production of the desired aromatic hydrocarbons, and reduce the need for increases in reactor temperature. Conversion is defined as the number of moles converted per mole of "convertible" components fed, as shown in Equations 1-3:

$$C6 \text{ conversion: } X_{C6} = \frac{\dot{n}_{conv\ C6,feed} - \dot{n}_{conv\ C6,prod}}{\dot{n}_{conv\ C6,feed}} \quad \text{Eq. 1}$$

$$C7 \text{ conversion: } X_{C7} = \frac{\dot{n}_{conv\ C7,feed} - \dot{n}_{conv\ C7,prod}}{\dot{n}_{conv\ C7,feed}} \quad \text{Eq. 2}$$

$$C6 + C7 \text{ conversion: } X_{C6+C7} = \quad \text{Eq. 3}$$
$$\frac{\dot{n}_{conv\ C6,feed} + \dot{n}_{conv\ C7,feed} - \dot{n}_{conv\ C6,prod} + \dot{n}_{conv\ C7,prod}}{\dot{n}_{conv\ C6,feed} + \dot{n}_{conv\ C7,feed}}$$

Additionally, the disclosed processes, reactor vessels, and reactor systems can result in unexpected increases in selectivity and yield when compared to the same process, vessel, or system without the membrane tube. In some embodiments, the (molar) selectivity to desired aromatic products, such as benzene, toluene, xylenes, or combinations thereof, can increase by at least 1%, at least 2%, at least 3%, and often up to 5-7%. Molar selectivities are defined in Equations 4-7:

$$\text{Benzene selectivity: } S_{Bz} = \frac{\dot{n}_{Bz,prod}}{\dot{n}_{conv\ C6,feed} - \dot{n}_{conv\ C6,prod}} \quad \text{Eq. 4}$$

$$\text{Toluene selectivity: } S_{Tol} = \frac{\dot{n}_{Tol,prod}}{\dot{n}_{conv\ C7,feed} - \dot{n}_{conv\ C7,prod}} \quad \text{Eq. 5}$$

$$\text{Benzene + Toluene selectivity: } S_{Bz+Tol} = \quad \text{Eq. 6}$$
$$\frac{\dot{n}_{Bz,prod} + \dot{n}_{Tol,prod}}{\dot{n}_{conv\ C6,C7,feed} - \dot{n}_{conv\ C6,C7,prod}}$$

$$\text{Aromatics selectivity: } S_{arom} = \frac{\dot{n}_{Bz,prod} + \dot{n}_{Tol,prod} + \dot{n}_{C8+arom,prod}}{\dot{n}_{conv\ C6-C8+,feed} - \dot{n}_{conv\ C6-C8+,prod}} \quad \text{Eq. 7}$$

Additionally or alternatively, the (molar) yield to desired aromatic products, such as benzene toluene, xylenes, or combinations thereof, can increase by at least 4%, at least 5%, or at least 6%, and often up to 10-15%, when compared to the same process, vessel, or system without the membrane tube. The aromatics yield is defined as moles $C_6$-$C_8$ aromatics formed divided by the convertible $C_6$-$C_8$ aromatics fed, and further, benzene yield, toluene yield, and benzene+toluene yield, are defined similarly.

Also unexpectedly, because increased conversion, increased yield, or both, generally results in a decrease in catalyst lifetime, the disclosed processes, reactor vessels, and reactor systems can result in a surprising increase in catalyst lifetime, for instance, of at least 1-5%, and in some instances, up to 10-15%, when compared to the same process, vessel, or system without the membrane tube. Therefore, a beneficial combination of increased conversion, increased yield, or both, with increased catalyst lifetime (or decreased catalyst deactivation) can be achieved.

In addition to these increases in conversion, selectivity, yield, and catalyst life, a decrease in undesired cracking reactions of at least 1%, at least 2%, at least 3%, and often up to 5-10% can result, when compared to the same process, vessel, or system without the membrane tube. Surprisingly, the removal of $H_2$ can selectively favor the production of desired aromatic hydrocarbons and reduce the production of cracked products, which utilize $H_2$ as a reactant.

EXAMPLES

The invention is further illustrated by the following examples, which are not to be construed in any way as imposing limitations to the scope of this invention. Various other aspects, embodiments, modifications, and equivalents thereof which, after reading the description herein, can suggest themselves to one of ordinary skill in the art without departing from the spirit of the present invention or the scope of the appended claims. In these examples, a representative aromatization reactor vessel system was evaluated, and the system included two aromatization reactor vessels in series with a membrane tube positioned between the reactor vessels.

The aromatization reactions were conducted in a pilot plant system with two aromatization reactors and a membrane tube arranged with Reactor 1 first, followed by the hydrogen membrane tube, and then Reactor 2. Typical reactor temperature set points were 850-975° F. Overall conversion with both reactors and without the membrane tube was 86-88% (mol % based on $C_6$), with about 50% conversion in Reactor 1 and about 36-38% conversion in Reactor 2. Each reactor employed 1-inch ID type 316 stainless steel in a vertical tubular reactor, and was loaded with 40 cc of whole extrudate Aromax® II Catalyst available from Chevron Phillips Chemical Company, LP (about 0.07 inch, screened to L/D of 2 to 3). Six thermocouples were equally spaced vertically in the catalyst bed. The term "catalyst temperature" as used herein is the catalyst average temperature (CAT), and is calculated from the six thermocouple temperatures as follows:

CAT=1/10(TC$_1$+TC$_6$)+1/5(TC$_2$+TC$_3$+TC$_4$+TC$_5$), where TC is the temperature of thermocouple C$_x$, and the thermocouples are arranged and numbered in order starting at the top of the catalyst bed. CAT is representative of the reactor temperature.

A commercial reformer startup procedure was simulated using the reactors described above. The gases, including evolved gases, were recycled. The startup included drying the catalyst in $N_2$ from room temperature to 500° F. for 79 hr at 57 psig, then heating the catalyst in a reducing mixture of 10% $H_2$ in $N_2$ from 500 to 932° F. at a rate of 10° F./hr over a period of about 43 hr, and then maintaining the catalyst at about 932° F. for 24 hr. The gas hourly space velocity (GHSV, which is the volume of gas at STP per volume of catalyst) was maintained at 1300 hr$^{-1}$ for the drying and reduction periods. The total elapsed time between catalyst loading and feed stream introduction was 146 hr.

The non-aromatic hydrocarbon used for these aromatization experiments was a hydrocarbon blend similar to that used in commercial catalytic reformers. The non-aromatic hydrocarbon contained only 1 wt. % of $C_9$ hydrocarbon, and was dried and hydrotreated to <50 ppb S. The sulfur content of the non-aromatic hydrocarbon was further reduced to <10 ppb by passing the non-aromatic hydrocarbon, along with recycle hydrogen, over a Pt-chlorided alumina catalyst layered over a sorbent of K on alumina at 650° F. in a pre-treatment zone located in front of the bound zeolitic aromatization catalyst. The non-aromatic hydrocarbon had the following composition ("-" is not detected):

| Carbon | Paraffins | Olefins | Naphthenes | Aromatics | Total |
| --- | --- | --- | --- | --- | --- |
| C3 | 0.0 | — | — | — | 0.0 |
| C4 | 0.1 | — | — | — | 0.1 |
| C5 | 1.6 | 0.0 | 0.7 | — | 2.2 |
| C6 | 60.0 | — | 0.7 | — | 60.7 |
| C7 | 24.0 | 0.0 | 1.2 | 1.7 | 27.0 |
| C8 | 8.5 | 0.1 | 0.0 | 0.0 | 8.7 |
| C9 | 0.6 | 0.2 | 0.1 | 0.1 | 1.0 |
| C10 | 0.1 | 0.0 | 0.0 | 0.0 | 0.1 |
| C11 | 0.0 | — | — | 0.0 | 0.0 |
| C12 | 0.0 | — | — | 0.0 | 0.0 |
| C15 | 0.0 | — | — | — | 0.0 |
| Total | 94.9 | 0.4 | 2.8 | 1.9 | 99.9 |

After completing the startup, the catalyst was cooled to approximately 800° F., and the feed stream was introduced. The feed stream to Reactor 1 was hydrogen and the non-aromatic hydrocarbon described above at a $H_2$:hydrocarbon ratio of 2:1, a LHSV of 1.6, and 67 mol % $H_2$ (partial pressure of $H_2$ of about 53 psia). Reactor 1 was operated at 65 psig and a CAT of 920° F. Approximately 50 mol % conversion was achieved in Reactor 1, and the discharge stream from Reactor 1 typically had a $H_2$:hydrocarbon ratio of 4:1 and 75 mol % $H_2$ (partial pressure of $H_2$ of about 60 psia). This discharge stream was fed through a pipe containing a membrane tube for hydrogen removal, prior to entering Reactor 2. The membrane tube was a shell/tube design palladium-silver alloy membrane.

The membrane tube was heated to maintain a temperature of 700° F. The stream leaving the process side of the membrane tube contained non-aromatic hydrocarbons, aromatic hydrocarbons, and hydrogen at a $H_2$:hydrocarbon ratio of 2:1 (partial pressure of $H_2$ of about 53 psia). The permeate side of the membrane tube was connected to a backpressure regulator, normally set at a pressure equal to the hydrogen partial pressure entering Reactor 1 (53 psia in this example), and an electronic flow meter to measure the amount of hydrogen removed via the membrane tube. The purity of this stream was >99 mol % $H_2$. Reactor 2 was operated at 65 psig and a CAT of 920° F.

The experimental methodology typically involved running for a period of about 100 hr using Reactor 1 and Reactor 2. Then, the membrane tube was brought on-line, and the discharge stream from Reactor 1 was contacted with the membrane tube (and a portion of the hydrogen removed) before entering Reactor 2.

Figure 7:
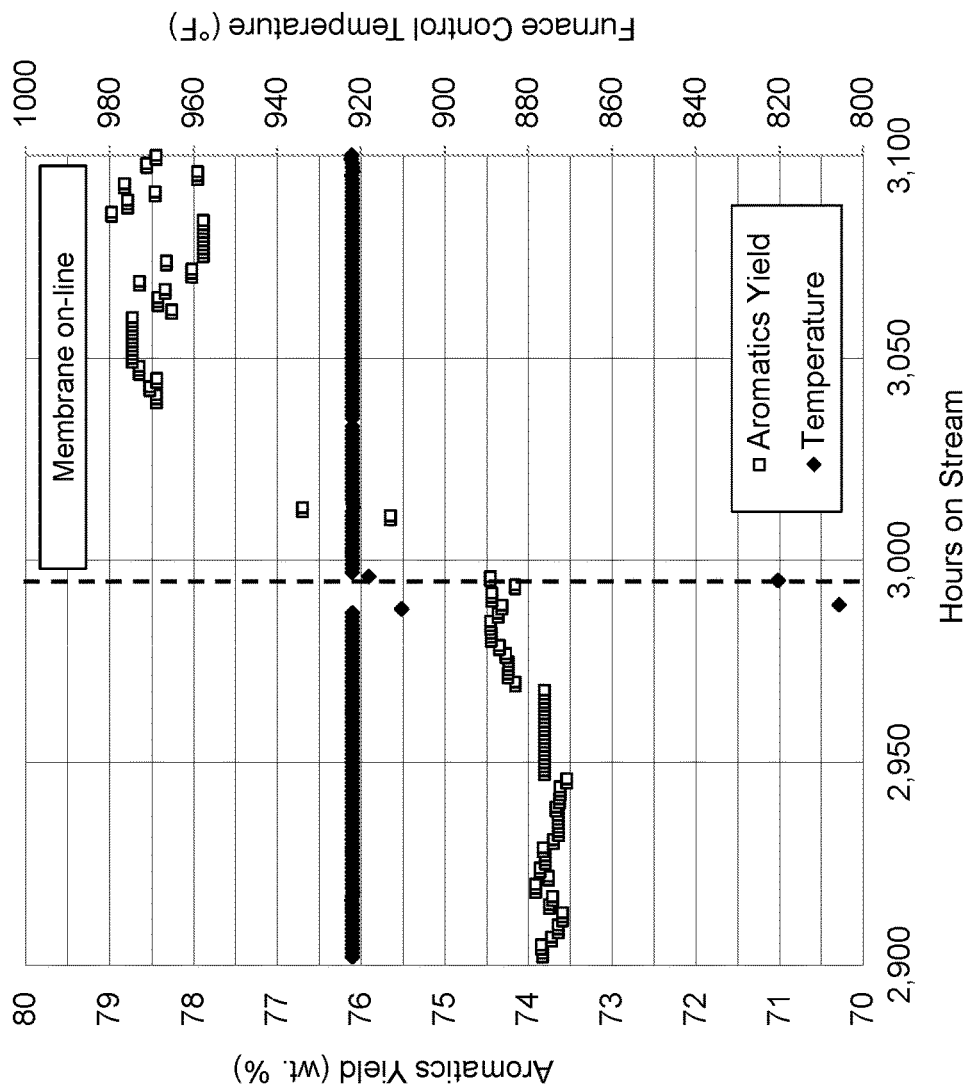
FIG. 7 is a plot of the yield of aromatic hydrocarbons and the reactor temperature versus time, both before and after a membrane tube was on-line.

FIG. 7 illustrates the unexpected increase in the aromatics yield (determined by gas chromatographic analysis) as a result of the membrane tube, which was brought on-line just before 3,000 hours. As shown in FIG. 7, at a constant reactor temperature of 920° F. and without the membrane tube, the yield of desired aromatic products (in wt. %) from 2,900 to just under 3,000 hours was 73.5-74.5 wt. %. After the membrane tube was brought on-line between Reactor 1 and Reactor 2, the yield of desired aromatic products surprisingly increased to 78-79 wt. %, an improvement of approximately 4.5 wt. %.

Figure 8:
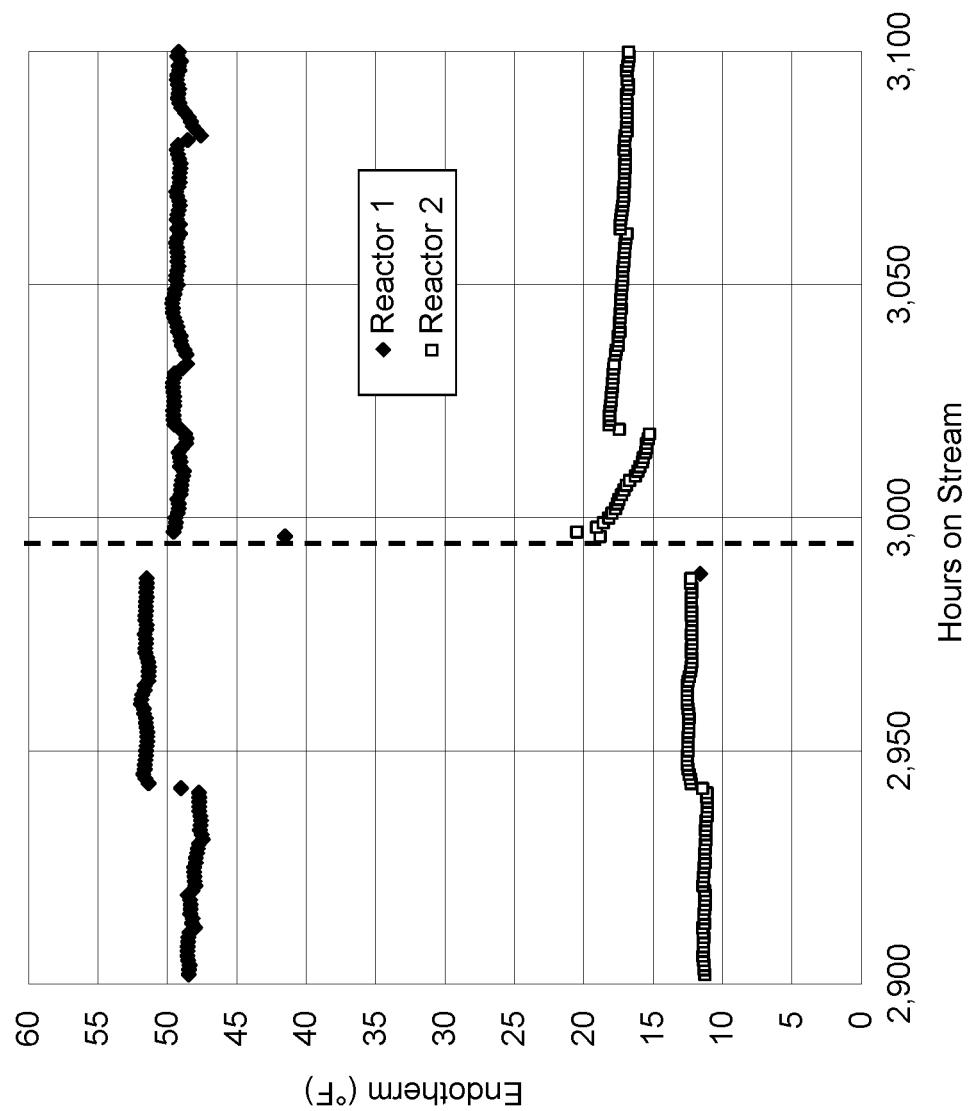
FIG. 8 is a plot of the reaction endotherms for Reactor 1 and Reactor 2, both before and after a membrane tube was on-line.

FIG. 8 demonstrates that the amount of the aromatization reaction occurring in Reactor 2 increased when the membrane tube was brought on-line. The reaction endotherm for Reactor 1 was consistent before and after the membrane tube was on-line. However, the reaction endotherm for Reactor 2 increased after the membrane tube was brought on-line, indicating that additional aromatization reaction was occurring in Reactor 2 when the hydrogen membrane tube was used (i.e., more conversion of non-aromatics to aromatics), as compared to when it was not used.

Figure 9:
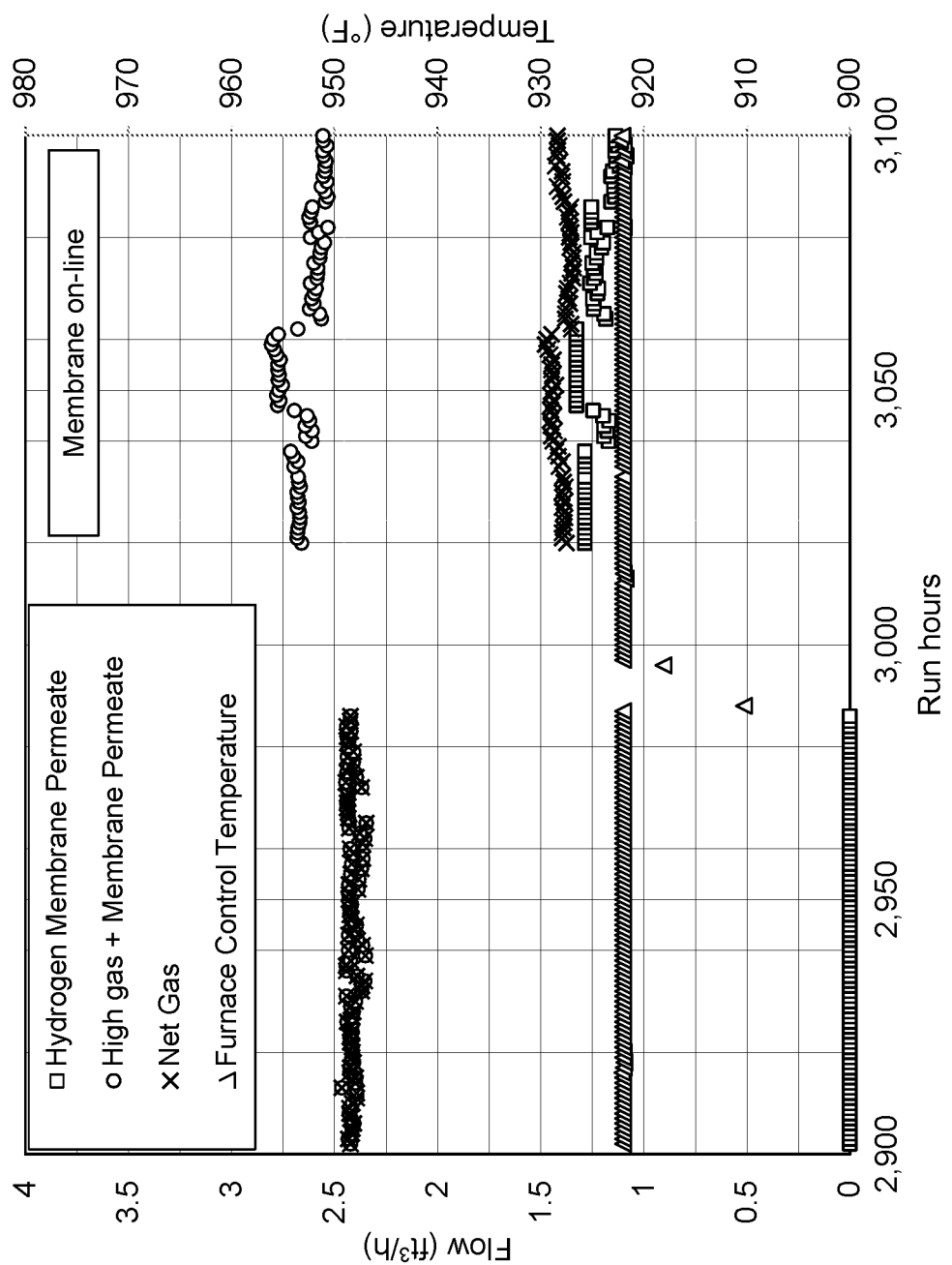
FIG. 9 is a plot of certain gas flow rates and the reactor temperature versus time, both before and after a membrane tube was on-line.

FIG. 9 illustrates various gas flow rates at a constant reactor temperature of 920° F., both before and after the membrane tube was on-line. Before the transition to membrane tube operation at about 3,000 hr, there was zero hydrogen membrane permeate flow, and the total gas flow rate was constant at a little less than about 2.5 ft³/hr. After the membrane tube was brought on-line, the total flow rate increased slightly to more than about 2.5 ft³/hr, however, approximately half of the hydrogen flow rate was removed in the hydrogen membrane permeate stream (about 1.25 ft³/hr). Thus, the membrane tube used in these experiments was effective at removing approximately 50% of the hydrogen.

Figure 10:
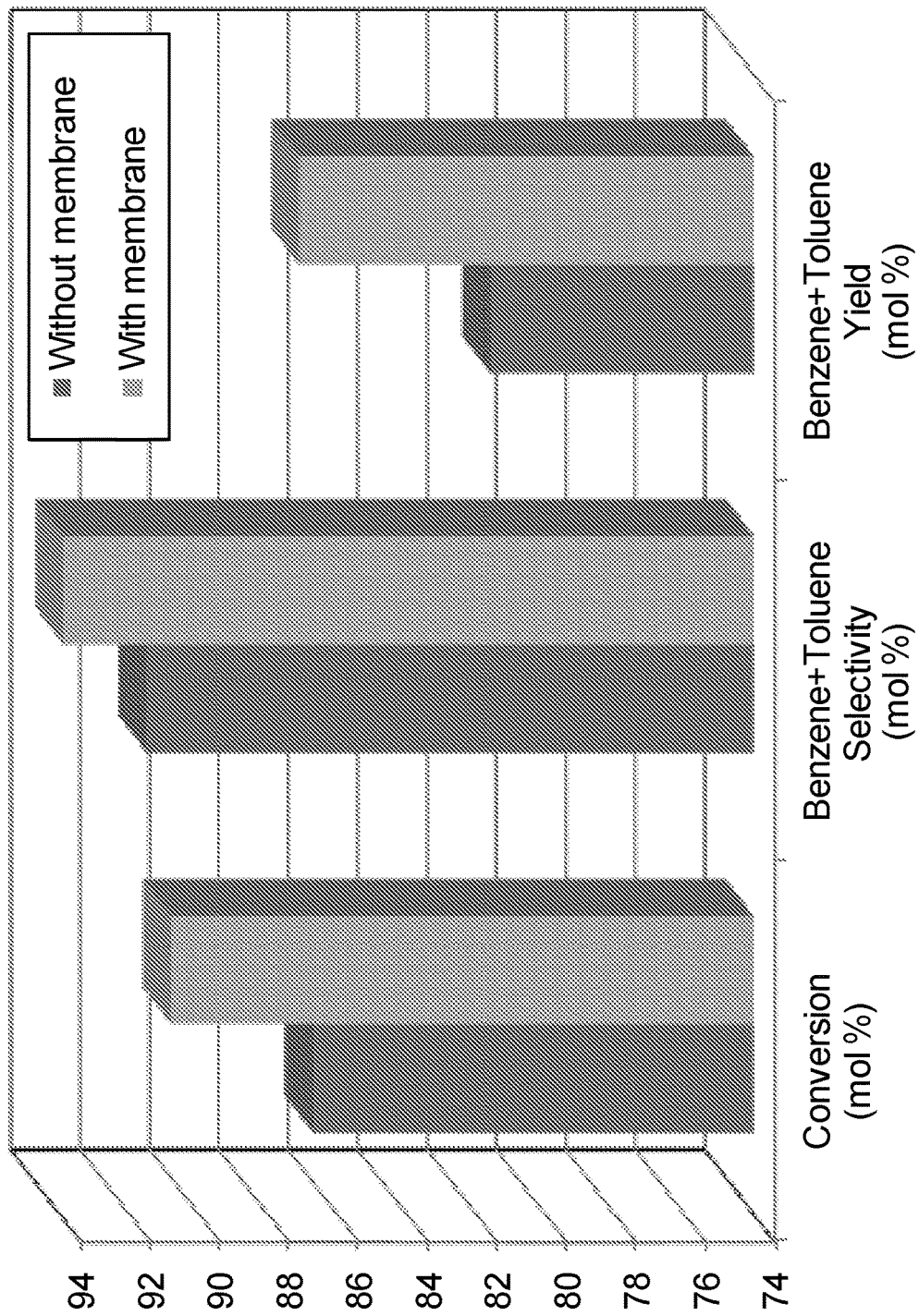
FIG. 10 is a chart summarizing the conversion, selectivity, and yield achieved with and without a membrane tube.

FIG. 10 summarizes the conversion, selectivity, and yield achieved with and without the hydrogen membrane tube (determined using gas chromatographic analysis). The conversion was 86 mol % without the membrane tube, and increased to 90 mol % with the use of the membrane tube. The selectivity (to desired benzene and toluene products) was about 90 mol % without the membrane tube, and increased to over 92 mol % with the use of the membrane tube, leading to a 2 mol % increase in selectivity. This increase in selectivity also can be used to estimate the decrease in undesired cracking reactions; therefore, the decrease in undesired cracking reactions (or side reactions) decreased by about 2 mol % as a result of the membrane tube. The yield (to desired benzene and toluene products) was about 80 mol % without the membrane tube, and increased to about 86 mol % with the use of the membrane tube. FIG. 10 demonstrates the significant and unexpected improvements in conversion, selectivity, and yield, and the reduction in cracking reactions, that can be achieved by the use of a membrane tube to remove hydrogen in an aromatization reactor system.

While the reactor system with the membrane tube was not on-line long enough to provide long-term catalyst lifetime data, it is believed that the catalyst lifetime was improved due to the removal of hydrogen via the membrane tube. This is also unexpected, as the prevailing theory was that more hydrogen was needed to improve catalyst lifetime by preventing the coke or carbonaceous build-up on the catalyst. Additionally, it is also believed that the ability to maintain conversion, selectivity, yield, or combinations thereof, but at a reduced reaction temperature due to the removal of hydrogen, can prolong catalyst lifetime. The invention is described above with reference to numerous aspects and embodiments, and specific examples. Many variations will suggest themselves to those skilled in the art in light of the above detailed description. All such obvious variations are within the full intended scope of the appended claims.

Embodiment 1

An aromatization reactor vessel comprising:
(a) a reactor wall;
(b) a catalyst bed positioned within the reactor vessel;
(c) an outer annulus positioned between the reactor wall and an outer particle barrier, the outer particle barrier and the outer annulus surrounding the catalyst bed;
(d) a reactor inlet for a feed stream;
(e) a reactor outlet connected to a center pipe, the center pipe positioned in the reactor vessel and surrounded by the catalyst bed;
  wherein a flow path for the feed stream begins at the reactor inlet, continues to the outer annulus, through the outer particle barrier and the catalyst bed, into the center pipe, and to the reactor outlet; and
(f) a membrane tube configured to remove $H_2$, the membrane tube positioned in the reactor vessel, the membrane tube having an inner permeate side and an outer process side.

Embodiment 2

The vessel defined in embodiment 1, wherein the membrane tube is positioned in the center pipe, and wherein the outer process side faces the center pipe.

Embodiment 3

The vessel defined in embodiment 1, wherein the membrane tube is positioned in the catalyst bed, and wherein the outer process side faces the catalyst bed.

Embodiment 4

The vessel defined in embodiment 1, wherein the membrane tube is positioned in the outer annulus, and wherein the outer process side faces the outer annulus.

Embodiment 5

The vessel defined in embodiment 4, wherein the outer annulus comprises scallops, and wherein at least one scallop is replaced with the membrane tube.

Embodiment 6

The vessel defined in embodiment 4, wherein the outer annulus comprises scallops, and wherein at least one scallop contains the membrane tube.

Embodiment 7

An aromatization reactor vessel comprising:
(a) a reactor wall;

(b) a catalyst bed positioned within the reactor vessel;
(c) an outer annulus positioned between the reactor wall and an outer particle barrier, the outer particle barrier and the outer annulus surrounding the catalyst bed;
(d) a reactor inlet for a feed stream;
(e) a reactor outlet connected to a center pipe, the center pipe positioned in the reactor vessel and surrounded by the catalyst bed;
  wherein a flow path for the feed stream begins at the reactor inlet, continues to the outer annulus, through the outer particle barrier and the catalyst bed, into the center pipe, and to the reactor outlet; and
(f) a membrane tube configured to remove $H_2$, the membrane tube positioned in the reactor outlet, wherein the membrane tube has an inner permeate side and an outer process side, the outer process side facing the reactor outlet.

Embodiment 8

An aromatization reactor vessel system comprising:
(I) an aromatization reactor vessel comprising:
  (a) a reactor wall;
  (b) a catalyst bed positioned within the reactor vessel;
  (c) an outer annulus positioned between the reactor wall and an outer particle barrier, the outer particle barrier and the outer annulus surrounding the catalyst bed;
  (d) a reactor inlet for a feed stream; and
  (e) a reactor outlet connected to a center pipe, the center pipe positioned in the reactor vessel and surrounded by the catalyst bed;
    wherein a flow path for the feed stream begins at the reactor inlet, continues to the outer annulus, through the outer particle barrier and the catalyst bed, into the center pipe, and to the reactor outlet; and
(II) a $H_2$ removal system configured to remove $H_2$ from a reactor effluent, the $H_2$ removal system positioned downstream of the reactor outlet, wherein:
  the $H_2$ removal system comprises a shell containing a membrane tube,
  the reactor effluent passes through the shell, and
  the membrane tube has an inner permeate side and an outer process side, the outer process side facing the shell.

Embodiment 9

An aromatization reactor vessel comprising:
(a) a reactor wall;
(b) a catalyst bed positioned within the reactor vessel;
(c) an outer annulus positioned between the reactor wall and an outer particle barrier, the outer particle barrier and the outer annulus surrounding the catalyst bed;
(d) a reactor inlet for a feed stream and connected to a center pipe, the center pipe positioned in the reactor vessel and surrounded by the catalyst bed;
(e) a reactor outlet (connected to the outer annulus);
  wherein a flow path for the feed stream begins at the reactor inlet, continues to the center pipe, through the catalyst bed and the outer particle barrier, into the outer annulus, and to the reactor outlet; and
(f) a membrane tube configured to remove $H_2$, the membrane tube positioned in the reactor vessel, the membrane tube having an inner permeate side and an outer process side.

Embodiment 10

The vessel defined in embodiment 9, wherein the membrane tube is positioned in the center pipe, and wherein the outer process side faces the center pipe.

Embodiment 11

The vessel defined in embodiment 9, wherein the membrane tube is positioned in the catalyst bed, and wherein the outer process side faces the catalyst bed.

Embodiment 12

The vessel defined in embodiment 9, wherein the membrane tube is positioned in the outer annulus, and wherein the outer process side faces the outer annulus.

Embodiment 13

The vessel defined in embodiment 12, wherein the outer annulus comprises scallops, and wherein at least one scallop is replaced with the membrane tube.

Embodiment 14

The vessel defined in embodiment 12, wherein the outer annulus comprises scallops, and wherein at least one scallop contains the membrane tube.

Embodiment 15

An aromatization reactor vessel comprising:
(a) a reactor wall;
(b) a catalyst bed positioned within the reactor vessel;
(c) an outer annulus positioned between the reactor wall and an outer particle barrier, the outer particle barrier and the outer annulus surrounding the catalyst bed;
(d) a reactor inlet for a feed stream and connected to a center pipe, the center pipe positioned in the reactor vessel and surrounded by the catalyst bed;
(e) a reactor outlet (connected to the outer annulus);
  wherein a flow path for the feed stream begins at the reactor inlet, continues to the center pipe, through the catalyst bed and the outer particle barrier, into the outer annulus, and to the reactor outlet; and
(f) a membrane tube configured to remove $H_2$, the membrane tube positioned in the reactor outlet, wherein the membrane tube has an inner permeate side and an outer process side, the outer process side facing the reactor outlet.

Embodiment 16

An aromatization reactor vessel system comprising:
(I) an aromatization reactor vessel comprising:
  (a) a reactor wall;
  (b) a catalyst bed positioned within the reactor vessel;
  (c) an outer annulus positioned between the reactor wall and an outer particle barrier, the outer particle barrier and the outer annulus surrounding the catalyst bed;

(d) a reactor inlet for a feed stream and connected to a center pipe, the center pipe positioned in the reactor vessel and surrounded by the catalyst bed; and (e) a reactor outlet (connected to the outer annulus); and wherein a flow path for the feed stream begins at the reactor inlet, continues to the center pipe, through the catalyst bed and the outer particle barrier, into the outer annulus, and to the reactor outlet; and (II) a $H_2$ removal system configured to remove $H_2$ from a reactor effluent, the $H_2$ removal system positioned downstream of the reactor outlet, wherein:

the $H_2$ removal system comprises a shell containing a membrane tube, the reactor effluent passes through the shell, and the membrane tube has an inner permeate side and an outer process side, the outer process side facing the shell.

Embodiment 17

The vessel or system defined in any one of the preceding embodiments, wherein the membrane tube is configured for an operating temperature in any suitable range or in any range disclosed herein, for example, at least 260° C., at least 400° C., at least 480° C., or from about 260° C. to about 600° C.

Embodiment 18

The vessel or system defined in any one of the preceding embodiments, wherein the membrane tube is configured for an operating pressure in any suitable range or in any range disclosed herein, for example, at least 20 psig, at least 30 psig, or from about 20 to about 100 psig.

Embodiment 19

The vessel or system defined in any one of the preceding embodiments, wherein the center pipe and the catalyst bed are positioned concentrically.

Embodiment 20

The vessel or system defined in any one of the preceding embodiments, wherein the center pipe comprises a screen or mesh section within the reactor vessel.

Embodiment 21

The vessel or system defined in any one of the preceding embodiments, wherein the center pipe comprises a coating/layer comprising any suitable metal or any metal disclosed herein (for example, tin) that provides resistance to carburization and metal dusting.

Embodiment 22

The vessel or system defined in any one of the preceding embodiments, wherein the reactor vessel comprises a coating/layer comprising any suitable metal or any metal disclosed herein (for example, tin) that provides resistance to carburization and metal dusting.

Embodiment 23

The vessel or system defined in any one of embodiments 1-22, wherein the reactor vessel is configured for decreasing temperature from the outer annulus to the center pipe.

Embodiment 24

The vessel or system defined in any one of embodiments 1-22, wherein the reactor vessel is configured for decreasing temperature from the center pipe to the outer annulus.

Embodiment 25

The vessel or system defined in any one of the preceding embodiments, wherein the outer annulus further comprises flow-affecting elements (for example, scallops, adjacent to the reactor wall) in the flow path to promote flow through or from the catalyst bed.

Embodiment 26

The vessel or system defined in any one of the preceding embodiments, wherein the reactor vessel is configured as a radial flow reactor.

Embodiment 27

The vessel or system defined in any one of the preceding embodiments, wherein the reactor vessel is a reactor vessel configured for a catalytic conversion of a non-aromatic hydrocarbon to an aromatic hydrocarbon (for example, benzene, toluene, or xylene).

Embodiment 28

The vessel or system defined in any one of the preceding embodiments, wherein the membrane tube has a generally cylindrical shape.

Embodiment 29

The vessel or system defined in any one of embodiments 1-28, wherein the membrane tube comprises (or is constructed of) any suitable transition metal or transition metal alloy, or any transition metal or transition metal alloy disclosed herein, for example, nickel, platinum, palladium, and the like.

Embodiment 30

The vessel or system defined in any one of embodiments 1-28, wherein the membrane tube comprises (or is constructed of) palladium Embodiment 31

The vessel or system defined in any one of embodiments 1-28, wherein the membrane tube comprises (or is constructed of) a polymer, ceramic, molecular sieve, or a combination thereof.

Embodiment 32

The vessel or system defined in any one of the preceding embodiments, wherein the membrane tube is stabilized with a mesh on the inner permeate side.

Embodiment 33

The vessel or system defined in any one of the preceding embodiments, wherein the membrane tube is protected by a screen on the outer process side.

Embodiment 34

The vessel or system defined in any one of the preceding embodiments, wherein the membrane tube is protected by one or more baffles on the outer process side.

Embodiment 35

The vessel or system defined in any one of the preceding embodiments, wherein the membrane tube is stabilized with a mesh comprising a coating/layer, the coating/layer comprising any suitable metal or any metal disclosed herein (for example, tin) that provides resistance to carburization and metal dusting.

Embodiment 36

The vessel or system defined in any one of the preceding embodiments, wherein the reactor vessel further comprises a top cover plate positioned at the top of the center pipe and the catalyst bed.

Embodiment 37

The vessel or system defined in any one of the preceding embodiments, wherein the reactor vessel further comprises an integrated heat exchange system around at least a portion of the reactor vessel for controlling temperature within the reactor vessel.

Embodiment 38

The vessel or system defined in any one of the preceding embodiments, wherein the vessel or system further comprises an electrical system for inducing an electrical bias across the membrane tube to control a $H_2$ removal rate.

Embodiment 39

The vessel or system defined in any one of the preceding embodiments, wherein the vessel or system further comprises a hydrocarbon analyzer to detect leaks on the inner permeate side of the membrane tube.

Embodiment 40

The vessel or system defined in any one of the preceding embodiments, wherein the vessel or system further comprises a $H_2$ backpressure system (for example, including a backpressure regulator) for controlling a $H_2$ partial pressure on the process side of the membrane tube.

Embodiment 41

The vessel or system defined in any one of the preceding embodiments, wherein an exit of the membrane tube is configured to provide a $H_2$ recycle stream or $H_2$ product stream having a purity of at least 95 mole % $H_2$.

Embodiment 42

The vessel or system defined in any one of the preceding embodiments, wherein the vessel or system further comprises a membrane bypass.

Embodiment 43

The vessel defined in any one of embodiments 1-7, 9-15, or 17-42, wherein more than one membrane tube is present in the reactor vessel, for example, configured in parallel.

Embodiment 44

The system defined in any one of embodiments 8 or 16-42, wherein the shell contains a plurality of membrane tubes, spaced apart from one another.

Embodiment 45

The system defined in any one of embodiments 8 or 16-42, wherein the shell contains a plurality of membrane tubes, aligned longitudinally in the shell and spaced apart from one another.

Embodiment 46

The system defined in embodiment 44 or 45, wherein the membrane tubes share a common exit port, for example, configured to provide a $H_2$ recycle stream or $H_2$ product stream having a purity of at least 95 mole % $H_2$.

Embodiment 47

The system defined in any one of embodiments 44-46, wherein the shell further comprises tube supports, spaced apart from the common exit port, the tube supports configured to stabilize the membrane tubes contained within the shell.

Embodiment 48

The system defined in any one of embodiments 44-47, wherein the shell further comprises flow-affecting elements (for example, baffles) to increase contact between the reactor effluent and the membrane tubes (for example, to promote turbulent flow).

Embodiment 49

An aromatization reactor vessel system comprising two or more aromatization reactor vessels in series, at least one of which is the aromatization reactor vessel defined in any one of embodiments 1-7, 9-15, or 17-43.

Embodiment 50

The system defined in embodiment 49, wherein the system comprises any suitable number of reactor vessels in series or any number of reactor vessels in series disclosed herein, for example, from 2 to 8 vessels in series, or 6 vessels in series.

Embodiment 51

The system defined in embodiment 49 or 50, wherein the aromatization vessel defined in any one of embodiments 1-7, 9-15, or 17-43 is the second, third, fourth, or fifth vessel in the series, or the third or fourth vessel in the series.

Embodiment 52

The system defined in any one of embodiments 49-51, wherein the aromatization vessel defined in any one of embodiments 1-7, 9-15, or 17-43 has an amount of catalyst less than the amount of catalyst in the next reactor vessel in the series.

Embodiment 53

The system defined in any one of embodiments 49-52, wherein the total amount of the catalyst in the aromatization vessel defined in any one of embodiments 1-7, 9-15, or 17-43 and each preceding reactor vessel in the series is in a range from about 10 to about 60 wt. %, based on the sum of the catalyst contained in all of the reactor vessels in the system.

Embodiment 54

The system defined in any one of embodiments 8, 16-42, or 44-48, wherein the system further comprises one or more additional aromatization vessels in series, wherein the $H_2$ removal system is positioned between two of the aromatization vessels.

Embodiment 55

The system defined in embodiment 54, wherein the system comprises any suitable number of reactor vessels in series or any number of reactor vessels in series disclosed herein, for example, from 2 to 8 vessels in series, or 6 vessels in series.

Embodiment 56

The system defined in embodiment 54 or 55, wherein the $H_2$ removal system is after the second, third, fourth, or fifth vessel in the series, or after the third or fourth vessel in the series.

Embodiment 57

The system defined in any one of embodiments 54-56, wherein the reactor vessel before the $H_2$ removal system has an amount of catalyst less than the amount of catalyst in the next reactor vessel in the series.

Embodiment 58

The system defined in any one of embodiments 54-57, wherein the total amount of the catalyst in the reactor vessels in the series before the $H_2$ removal system is in a range from about 10 to about 60 wt. %, based on the sum of the catalyst contained in all of the reactor vessels in the system.

Embodiment 59

The system defined in any one of embodiments 49-58, further comprising a furnace before each reactor vessel, the furnace capable of reheating a feed stream to a reactor vessel operating temperature of from about 350° C. to about 600° C.

Embodiment 60

The system defined in any one of embodiments 49-58, further comprising a furnace before the first reactor vessel in the series.

Embodiment 61

The system defined in any one of embodiments 49-58, further comprising a furnace before each reactor vessel, each furnace configured to heat a reactor effluent of the previous reactor vessel to a temperature, independently, of from about 350° C. to about 600° C. before entering the next vessel in the series.

Embodiment 62

The system defined in any one of embodiments 49-61, wherein $H_2$ from the membrane tube (or exit port) is used as a component of a feed stream to another reactor vessel in the series (for example, the first reactor), and has a purity of at least 95 mole % $H_2$.

Embodiment 63

The system defined in any one of embodiments 49-62, wherein $H_2$ from the membrane tube (or exit port) is a product stream (for example, to a cyclohexane production system), and has a purity of at least 95 mole % $H_2$.

Embodiment 64

The system defined in any one of embodiments 49-63, wherein $H_2$ from the membrane tube (or exit port) is reacted with any suitable unsaturated hydrocarbon disclosed herein (for example, benzene over a hydrogenation catalyst to produce cyclohexane); is used in a refinery to upgrade hydrocarbons either by hydrotreating oil fractions to remove sulfur, nitrogen, or both; or is used in any suitable chemical process or refinery process.

Embodiment 65

The system defined in any one of embodiments 49-64, wherein the system is configured for a single pass through each reactor vessel in the series.

Embodiment 66

An aromatization reactor vessel system comprising a series of two or more furnace-reactor pairs, each pair connected by a transfer pipe, wherein a membrane tube configured to remove $H_2$ is positioned in at least one transfer pipe, and wherein the membrane tube has an inner permeate side and an outer process side, the outer process side facing the transfer pipe.

Embodiment 67

The system defined in embodiment 66, wherein the reactor vessel of the furnace-reactor pair and the membrane tube are further characterized as defined in any one of embodiments 1-7, 9-15, or 17-43.

Embodiment 68

An aromatization reactor vessel system comprising a series of two or more furnace-reactor pairs, each pair connected by a transfer pipe, wherein a $H_2$ removal system configured to remove $H_2$ is connected to at least one transfer pipe, and wherein the $H_2$ removal system comprises a shell containing a membrane tube, the membrane tube having an inner permeate side and an outer process side, the outer process side facing the shell.

Embodiment 69

The system defined in embodiment 68, wherein the reactor vessel of the furnace-reactor pair and the $H_2$ removal system are further characterized as defined in any one of embodiments 8, 16-42, or 44-48.

Embodiment 70

An aromatization process comprising:
(i) introducing a feed stream comprising $H_2$ and a non-aromatic hydrocarbon into the reactor inlet and the flow path of the reactor vessel or system of any one of embodiments 1-69;
(ii) contacting the feed stream with an aromatization catalyst;
(iii) catalytically converting at least a portion of the non-aromatic hydrocarbon within the reactor vessel to produce an aromatic hydrocarbon and $H_2$;
(iv) discharging a reactor effluent comprising the aromatic hydrocarbon from the reactor vessel via the reactor outlet; and
(v) removing a portion of the $H_2$ from within the reactor vessel (or from the reactor outlet, or from the reactor effluent) via the membrane tube to reduce a partial pressure of $H_2$ in the process, for example, a $H_2$:hydrocarbon ratio reduction of from about 4:1-5:1 to about 1.5:1-2:1 (in this ratio of $H_2$:hydrocarbon, the "hydrocarbon" includes both aromatic hydrocarbons and non-aromatic hydrocarbons, but excludes cracked products of lower carbon numbers ($C_1$-$C_4$)).

Embodiment 71

The process defined in embodiment 70, wherein the aromatization catalyst comprises a Group 7-11 transition metal deposited on an inorganic support.

Embodiment 72

The process defined in embodiment 71, wherein the Group 7-11 transition metal comprises platinum, rhenium, gold, or combinations thereof.

Embodiment 73

The process defined in embodiment 70, wherein the aromatization catalyst comprises a group 14 metal (for example, tin).

Embodiment 74

The process defined in embodiment 71, wherein the inorganic support comprises an alumina or aluminosilicate support.

Embodiment 75

The process defined in embodiment 71, wherein the inorganic support comprises a zeolitic support (for example, a L-zeolite).

Embodiment 76

The process defined in embodiment 70, wherein the aromatization catalyst comprises one or more halogens.

Embodiment 77

The process defined in any one of embodiments 70-76, wherein the non-aromatic hydrocarbon comprises hexane, heptane, or a combination thereof.

Embodiment 78

The process defined in any one of embodiments 70-77, wherein the aromatic hydrocarbon comprises benzene, toluene, or a combination thereof.

Embodiment 79

The process defined in any one of embodiments 70-78, wherein the process reduces undesired cracking reactions, for example, by any amount disclosed herein.

Embodiment 80

The process defined in any one of embodiments 70-79, wherein the process increases conversion, selectivity, yield, or combinations thereof, for example, by any amount disclosed herein, when compared to the same process, vessel, or system without the membrane tube (for example, with the membrane tube disabled).

Embodiment 81

The process defined in any one of embodiments 70-80, wherein the process increases conversion by at least 2 mol %, when compared to the same process, vessel, or system without the membrane tube.

Embodiment 82

The process defined in any one of embodiments 70-81, wherein the process increases selectivity by at least 1 mol %, when compared to the same process, vessel, or system without the membrane tube.

Embodiment 83

The process defined in any one of embodiments 70-82, wherein the yield of desired aromatic products increases by at least 4 mol %, when compared to the same process, vessel, or system without the membrane tube.

Embodiment 84

The process defined in any one of embodiments 70-83, wherein the process increases catalyst lifetime, for example, by any amount disclosed herein.

Embodiment 85

The process defined in any one of embodiments 70-84, wherein the $H_2$:hydrocarbon molar ratio in step (v), after $H_2$ removal, is any range disclosed herein, for example, from about 1:1 to about 2:1, or from about 1.5:1 to about 2:1.

Embodiment 86

The process defined in any one of embodiments 70-85, wherein steps (ii) and (iii) are conducted at a pressure in a range from about 20 to about 100 psig.

Embodiment 87

The process defined in any one of embodiments 70-86, wherein steps (ii) and (iii) are conducted a temperature in a range from about 350° C. to about 600° C.

Embodiment 88

The process defined in any one of embodiments 70-87, wherein the non-aromatic hydrocarbon conversion prior to the removing step is in a range from about 50 to about 90%.

We claim:

1. An aromatization reactor vessel comprising:
   (a) a reactor wall;
   (b) a catalyst bed positioned within the reactor vessel;
   (c) an outer annulus positioned between the reactor wall and an outer particle barrier, the outer particle barrier and the outer annulus surrounding the catalyst bed;
   (d) a reactor inlet for a feed stream;
   (e) a reactor outlet connected to a center pipe, the center pipe positioned in the reactor vessel and surrounded by the catalyst bed;
      wherein a flow path for the feed stream begins at the reactor inlet, continues to the outer annulus, through the outer particle barrier and the catalyst bed, into the center pipe, and to the reactor outlet; and
   (f) a membrane tube configured to remove $H_2$, the membrane tube positioned in the center pipe or the outer annulus, the membrane tube having an inner permeate side and an outer process side.

2. The vessel of claim 1, wherein the membrane tube is positioned in the center pipe, and wherein the outer process side faces the center pipe.

3. The vessel of claim 1, wherein the membrane tube is positioned in the outer annulus, and wherein the outer process side faces the outer annulus.

4. The vessel of claim 1, wherein the membrane tube is configured for an operating temperature in a range from about 260° C. to about 600° C.

5. The vessel of claim 1, wherein the membrane tube comprises palladium.

6. The vessel of claim 1, wherein the center pipe and the catalyst bed are positioned concentrically.

7. The vessel of claim 1, wherein the aromatization reactor vessel is configured for a catalytic conversion of a non-aromatic hydrocarbon to an aromatic hydrocarbon comprising benzene, toluene, xylene, or combinations thereof.

8. An aromatization reactor vessel system comprising from two to eight aromatization reactor vessels in series, wherein at least one is the aromatization reactor vessel of claim 1.

9. The system of claim 8, wherein the aromatization reactor vessel system is configured to increase selectivity and to increase catalyst lifetime, as compared to an equivalent aromatization reactor vessel system without the membrane tube, under the same reaction conditions.

10. The vessel of claim 1, wherein the vessel further comprises an electrical system for inducing an electrical bias across the membrane tube to control a $H_2$ removal rate.

11. An aromatization reactor vessel system comprising from 2 to 8 aromatization reactor vessels in series, wherein at least one is an aromatization reactor vessel comprising:
   (a) a reactor wall;
   (b) a catalyst bed positioned within the reactor vessel;
   (c) an outer annulus positioned between the reactor wall and an outer particle barrier, the outer particle barrier and the outer annulus surrounding the catalyst bed;
   (d) a reactor inlet for a feed stream;
   (e) a reactor outlet connected to a center pipe, the center pipe positioned in the reactor vessel and surrounded by the catalyst bed;
      wherein a flow path for the feed stream begins at the reactor inlet, continues to the outer annulus, through the outer particle barrier and the catalyst bed, into the center pipe, and to the reactor outlet; and
   (f) a membrane tube configured to remove $H_2$, the membrane tube positioned in the reactor outlet, wherein the membrane tube has an inner permeate side and an outer process side, the outer process side facing the reactor outlet;
   wherein a total amount of the catalyst in the aromatization reactor vessel containing the membrane tube and each preceding reactor vessel in the series is in a range from about 15 to about 50 wt. %, based on the sum of the catalyst contained in all of the reactor vessels in the system.

12. The system of claim 11, wherein the aromatization reactor vessel system is configured to increase selectivity, as compared to an equivalent aromatization reactor vessel system without the membrane tube, under the same reaction conditions.

13. The system of claim 11, wherein the aromatization reactor vessel system is configured to increase catalyst lifetime, as compared to an equivalent aromatization reactor vessel system without the membrane tube, under the same reaction conditions.

14. The system of claim 11, wherein:
   the system comprises from 4 to 7 aromatization reactor vessels in series; and
   the total amount of the catalyst in the aromatization reactor vessel containing the membrane tube and each preceding reactor vessel in the series is in a range from about 20 to about 45 wt. %, based on the sum of the catalyst contained in all of the reactor vessels in the system.

15. An aromatization reactor vessel system comprising:
   (I) an aromatization reactor vessel comprising:
      (a) a reactor wall;
      (b) a catalyst bed positioned within the reactor vessel;
      (c) an outer annulus positioned between the reactor wall and an outer particle barrier, the outer particle barrier and outer annulus surrounding the catalyst bed;
      (d) a reactor inlet for a feed stream; and
      (e) a reactor outlet connected to a center pipe, the center pipe positioned in the reactor vessel and surrounded by the catalyst bed;
         wherein a flow path for the feed stream begins at the reactor inlet, continues to the outer annulus, through the outer particle barrier and the catalyst bed, into the center pipe, and to the reactor outlet; and
   (II) a $H_2$ removal system configured to remove $H_2$ from a reactor effluent, wherein a $H_2$:hydrocarbon molar ratio in the reactor effluent is reduced from within a range of about 4:1 to about 5:1 to within a range from about 1.5:1 to about 2:1, the $H_2$ removal system positioned downstream of the reactor outlet, wherein:
      the $H_2$ removal system comprises a shell containing a membrane tube,
      the reactor effluent passes through the shell, and
      the membrane tube has an inner permeate side and an outer process side, the outer process side facing the shell.

16. The system of claim 15, wherein the shell contains a plurality of membrane tubes, spaced apart from one another, and wherein the membrane tubes share a common exit port configured to provide a $H_2$-containing stream having a purity of at least 95 mole % $H_2$.

17. The system of claim 16, wherein the shell further comprises tube supports, the tube supports configured to stabilize the membrane tubes contained within the shell.

18. The system of claim 15, wherein the system comprises the aromatization reactor vessel and from one to seven additional aromatization reaction vessels, configured in series, wherein the $H_2$ removal system is positioned between any two reactor vessels.

19. The system of claim 18, wherein the $H_2$ removal system is after the third or fourth vessel in the series.

20. The system of claim 19, wherein the aromatization reactor vessel before the $H_2$ removal system has an amount of catalyst less than an amount of catalyst in the next reactor vessel in the series.

* * * * *